(12) United States Patent
Visco et al.

(10) Patent No.: US 8,332,028 B2
(45) Date of Patent: Dec. 11, 2012

(54) PROTECTED LITHIUM ELECTRODES FOR ELECTRO-TRANSPORT DRUG DELIVERY

(75) Inventors: Steven J. Visco, Berkeley, CA (US); Yevgeniy S. Nimon, Danville, CA (US); Bruce Katz, Berkeley, CA (US)

(73) Assignee: PolyPlus Battery Company, Berkeley, CA (US)

( * ) Notice: Subject to any disclaimer, the term of this patent is extended or adjusted under 35 U.S.C. 154(b) by 683 days.

(21) Appl. No.: 11/946,791

(22) Filed: Nov. 28, 2007

(65) Prior Publication Data

US 2008/0161746 A1 Jul. 3, 2008

Related U.S. Application Data

(60) Provisional application No. 60/867,553, filed on Nov. 28, 2006, provisional application No. 60/970,729, filed on Sep. 7, 2007.

(51) Int. Cl.
*A61N 1/30* (2006.01)
*A61F 2/00* (2006.01)
*A61F 13/00* (2006.01)
*A61K 9/70* (2006.01)
*A61K 33/00* (2006.01)
*A61K 9/22* (2006.01)
*A01N 59/00* (2006.01)

(52) U.S. Cl. .......... 604/20; 424/424; 424/425; 424/449; 424/722; 604/890.1; 604/891.1

(58) Field of Classification Search ........... 604/20, 604/890.1, 891.1, 501, 502; 424/424, 425, 424/449, 722
See application file for complete search history.

(56) References Cited

U.S. PATENT DOCUMENTS

| | | | |
|---|---|---|---|
| 4,477,971 A | 10/1984 | Jacobsen et al. | |
| 4,585,652 A | 4/1986 | Miller et al. | |
| 4,731,049 A | 3/1988 | Parsi | |
| 4,744,787 A | 5/1988 | Phipps et al. | |
| 4,747,819 A | 5/1988 | Phipps et al. | |
| 4,856,188 A | 8/1989 | Sibalis | |
| 4,915,685 A | 4/1990 | Petelenz et al. | |
| 4,973,303 A | 11/1990 | Johnson et al. | |
| 4,985,317 A * | 1/1991 | Adachi et al. | 429/322 |
| 5,035,963 A * | 7/1991 | Plichta et al. | 429/103 |

(Continued)

OTHER PUBLICATIONS

Nemeroff Charles, et al., "Treatment of mood disorders", *Nature Neuroscience Supplement*, vol. 5, Nov. 2002, pp. 1068-1070.

(Continued)

*Primary Examiner* — Kevin C Sirmons
*Assistant Examiner* — Shefali Patel
(74) *Attorney, Agent, or Firm* — Weaver Austin Villeneuve & Sampson LLP

(57) ABSTRACT

This invention provides new and novel devices and methods for administering lithium (Li) ions to a mammalian subject, especially delivery of the lithium (Li) ions to a body component for example across a body or tissue surface such as skin or a mucosal membrane, or for the delivery of the lithium ions directly to bodily fluids in a controllable and reproducible manner. In certain embodiments the device comprises a donor electrode that is a donor of the lithium ions; a protective architecture that is ionically conductive to the lithium ions, configured for application to a skin surface and positioned to isolate said donor electrode from the skin surface; and a counter electrode configured for application to the skin surface, where said counter electrode is operably coupled to said donor electrode.

37 Claims, 8 Drawing Sheets

U.S. PATENT DOCUMENTS

| | | | |
|---|---|---|---|
| 5,135,477 A | 8/1992 | Untereker et al. | |
| 5,162,042 A | 11/1992 | Gyory et al. | |
| 5,288,503 A | 2/1994 | Wood et al. | |
| 5,322,520 A | 6/1994 | Milder | |
| 5,395,310 A | 3/1995 | Unterecker et al. | |
| 5,405,317 A | 4/1995 | Myers et al. | |
| 5,415,628 A | 5/1995 | Untereker et al. | |
| 5,525,442 A * | 6/1996 | Shuster | 429/320 |
| 5,573,503 A | 11/1996 | Untereker et al. | |
| 5,622,530 A | 4/1997 | Phipps | |
| 5,685,837 A | 11/1997 | Horstmann | |
| 5,711,761 A | 1/1998 | Untereker et al. | |
| 5,857,992 A * | 1/1999 | Haak et al. | 604/20 |
| 5,935,598 A | 8/1999 | Sage et al. | |
| 5,965,154 A | 10/1999 | Michalik | |
| 5,972,377 A | 10/1999 | Jona et al. | |
| 6,004,309 A | 12/1999 | Phipps | |
| 6,025,094 A | 2/2000 | Visco et al. | |
| 6,207,182 B1 | 3/2001 | Raimondi | |
| 6,214,061 B1 | 4/2001 | Visco et al. | |
| 6,289,241 B1 | 9/2001 | Phipps | |
| 6,350,259 B1 | 2/2002 | Sage, Jr. et al. | |
| 6,375,990 B1 * | 4/2002 | Nemeroff et al. | 424/667 |
| 6,402,795 B1 | 6/2002 | Chu et al. | |
| 6,413,284 B1 | 7/2002 | Chu et al. | |
| 6,413,285 B1 | 7/2002 | Chu et al. | |
| 6,635,045 B2 | 10/2003 | Keusch et al. | |
| 6,745,071 B1 | 6/2004 | Anderson et al. | |
| 6,955,866 B2 | 10/2005 | Nimon et al. | |
| 6,989,159 B2 | 1/2006 | Tarro | |
| 7,016,723 B2 | 3/2006 | Morris et al. | |
| 7,122,272 B2 | 10/2006 | Okawa et al. | |
| 7,282,295 B2 | 10/2007 | Visco et al. | |
| 7,282,296 B2 | 10/2007 | Visco et al. | |
| 7,282,302 B2 | 10/2007 | Visco et al. | |
| 2002/0016562 A1 | 2/2002 | Cormier et al. | |
| 2002/0068220 A1 * | 6/2002 | Wyler et al. | 429/231 |
| 2002/0106563 A1 * | 8/2002 | Okawa et al. | 429/221 |
| 2002/0160056 A1 | 10/2002 | Nemeroff et al. | |
| 2003/0088204 A1 | 5/2003 | Joshi | |
| 2003/0124433 A1 * | 7/2003 | Kim et al. | 429/324 |
| 2004/0126653 A1 | 7/2004 | Visco et al. | |
| 2004/0185334 A1 * | 9/2004 | Iwamoto | 429/127 |
| 2004/0191617 A1 | 9/2004 | Visco et al. | |
| 2004/0197641 A1 * | 10/2004 | Visco et al. | 429/137 |
| 2005/0004550 A1 * | 1/2005 | Sun et al. | 604/501 |
| 2007/0211413 A1 | 9/2007 | Fife et al. | |
| 2009/0005824 A1 | 1/2009 | Visco et al. | |
| 2009/0069740 A1 | 3/2009 | Visco et al. | |

OTHER PUBLICATIONS

Lattin Gary, et al., "Electronic Control of Iontophoretic Drug Delivery", *Annals New York Academy of Sciences*, 1991, ISSN00778923, vol. 618, pp. 450-464.

Phipps J.B., et al., "Transport of Ionic Species Through Skin", *Solid State Ionics*, 28-30 (1988) pp. 1778-1783.

Phipps J.B., et al., "Transdermal ion migration", *Advanced Drug Delivery Reviews*, 9 (1992), pp. 137-176.

Phipps J.B., et al., "Iontophoretic Delivery of Model Inorganic and Drug Ions", *Journal of Pharmaceutical Sciences*, vol. 78, No. 5, May 1989, pp. 365-369.

Sahota Tarsem S., et al., "In Vitro Iontophoretic Release of Lithium Chloride and Lidocaine Hydrochloride from Polymer Electrolytes", *Drug Development and Industrial Pharmacy*, 26(10), (2000) pp. 1039-1044.

Linford Roger, et al., "Drug Delivery and Solid State Ionics", Abstract No. 93, downloaded from http://www.ssi-15.net/doc/Abstract_Linford on Sep. 29, 2006, pp. 1-2.

Latham R.J., et al., "The Role of Polymer Electrolytes in Drug Delivery", *Solid State Ionics: Trends in the New Millennium*, 2002 pp. 283-293.

Costello Charles, et al., "Iontophoresis: Applications in Transdermal Medication Delivery", *Physical Therapy*, vol. 75, No. 6, Jun. 1995, pp. 554-562.

Pilcher Helen R., "The ups and downs of lithium", *Nature*, vol. 425, Sep. 11, 2003, pp. 118-120.

Segal Menahem, "Lithium and the monoamine neurotransmitters in the rat hippocampus", *Nature*, vol. 250, Jul. 5, 1974, downloaded from http://www.nature.com on Sep. 28, 2006, pp. 1-2.

Case archive, Nephrology, "Lithium Toxicity Leads to Kidney Failure", *MedQuest*, downloaded from http://www.medquest.com on Oct. 10, 2006, one page.

"Going to Extremes: Bipolar Disorder", *National Institute of Mental Health*, downloaded from http://www.nimh.nih.gov on Oct. 9, 2006, pp. 1-4.

Baldessarini Ross J., et al., "Does Lithium Treatment Still Work?", *JAMA & Archives, Archives of General Psychiatry*, downloaded from http://archpsyc.ama-assn.org on Sep. 28, 2006, pp. 1-2.

"Efficacy of lithium: History of the Introduction of Lithium", downloaded from http://www.uea.ac.uk on May 18, 2007, pp. 1-2.

Aggrawal Anil, "Anil Aggrawal's Internet journal of Forensic Medicine and Toxicology—Introduction and History—Lithium Toxicity A Review", vol. 1, No. 2, Jul.-Dec. 2000, downloaded from http://www.geradts.com on May 18, 2007, pp.

"Toxicity, Lithium", *EMedicine from WebMD*, downloaded from http://www.emedicine.com on Oct. 9, 2006, pp. 1-7.

Durbano F., et al. "The long-term efficacy and tolerability of carbolithium once a day: an interim analysis at 6 months", *NCBI PubMed*, downloaded from http://www.ncbi.nim.nih.gov on Oct. 10, 2006, pp. 1-2.

WO patent application No. PCT/US2008/068671, International Search Report and Written Opinion dated Jan. 29, 2009.

U.S. Appl. No. 12/204,672, "Protected Donor Electrodes for Electro-Transport Drug Delivery", Visco et al., filed Sep. 4, 2008.

U.S. Appl. No. 12/163,821, "Electrotransport Devices, Methods and Drug Electrode Assemblies", Visco et al., filed Jun. 27, 2008.

International patent application No. PCT/US2007/085802, International Search Report dated May 23, 2008.

International patent application No. PCT/US2007/085802, Written Opinion dated May 23, 2008.

U.S. Appl. No. 12/163,821, Office Action mailed Aug. 23, 2011.
U.S. Appl. No. 12/204,672, Office Action mailed Nov. 25, 2011.
U.S. Appl. No. 12/163,821, Office Action mailed Feb. 7, 2012.
U.S. Appl. No. 12/204,672, Office Action mailed Jul. 22, 2009.
U.S. Appl. No. 12/204,672, Office Action mailed Mar. 24, 2010.
U.S. Appl. No. 12/163,821, Office Action mailed Aug. 9, 2010.
U.S. Appl. No. 12/163,821, Office Action mailed Jan. 20, 2011.

* cited by examiner

PROTECTED LITHIUM ELECTRODES FOR ELECTRO-TRANSPORT DRUG DELIVERY

CROSS-REFERENCE TO RELATED APPLICATIONS

This application claims priority to U.S. Provisional Patent Application No. 60/867,553 filed Nov. 28, 2006, titled LITHIUM ELECTRODES FOR ELECTRO-TRANSPORT DRUG DELIVERY and U.S. Provisional Patent Application No. 60/970,729 filed Sep. 7, 2007, titled PROTECTED LITHIUM ELECTRODES FOR ELECTRO-TRANSPORT DRUG DELIVERY. Each of these prior applications is incorporated herein by reference in its entirety and for all purposes.

FIELD OF THE INVENTION

This invention relates to electro-transport drug delivery of lithium to a mammalian subject. More particularly, in certain embodiments, this invention relates to electro-transport devices and methods for administering therapeutic doses of lithium to a subject for treatment by transporting Li ions across a body surface such as skin or mucosal membrane.

BACKGROUND OF THE INVENTION

The use of transdermal patches for time-released drug delivery is well known in the medical community. Transdermal patches are used to deliver a wide variety of pharmaceuticals including estrogen, nicotine, lidocaine and other molecules that are able to pass through the skin (see, e.g., U.S. Pat. Nos. 5,965,154, 5,972,377, 6,207,182, and the like). The controlled release of drugs offers advantages over oral and/or injected medications in terms of convenience and more importantly, the maintenance of a steady therapeutic concentration of medicament.

Oral doses of lithium salts including lithium carbonate and lithium citrate are well known for the treatment of bipolar disorder. Unfortunately the blood concentration of lithium ion ($Li^+$) changes rather sharply over time after ingestion of the lithium salt. The typical blood volume for a human is about 5 liters. According to the National Institute of Health (NIH) (see, e.g., website://dailymed.nlm.nih.gov/dailymed/about.cfm), the target value for treatment of bipolar disorder is approximately 0.6 to 1.2 mEq/l. Given a total blood volume of 5 liters, the total lithium dosage for treatment of biopolar disorder is about 3 to 6 mEq which translates to 21 to 42 milligrams of lithium (metal). Assuming an average uptake of 30 mg $Li^+$ every 12 hours (60 mg/day), a lithium patch supplying $Li^+$ for one week (14 doses) would need 420 mg of lithium metal (less than half a gram). If the lithium source were a lithium carbonate salt (mol wt.=73.89), one would need 111 to 222 mg of $Li_2CO_3$ to achieve the therapeutic concentration of 3 to 6 mEq, respectively. So a one-week lithium patch having a $Li_2CO_3$ salt as the source of lithium would require at least 1554 to 3108 mg of salt.

When taken orally, a typical dosage is around 300 mg of $Li_2CO_3$ to achieve the therapeutic target of 3 to 6 mEq of $Li^+$. Unfortunately, the therapeutic value for lithium is very close to the toxic threshold, and there is no known antidote for lithium poisoning.

The idea for a lithium transdermal patch is described in Raimondi (U.S. Pat. No. 6,207,182), where a simple adhesive patch containing a lithium salt is used for delivery of lithium. There are problems with this approach, notably the large amount (volume) of lithium salt necessary for treatment of bipolar disorder, leading to a cumbersome patch. Also, using the simple patch in Raimondi lithium uptake rates may not be sufficient to provide effective treatment.

The use of iontophoresis for transdermal lithium delivery is described by Nemeroff et al. (U.S. Pat. No. 6,375,990). However, this device suffers from the same problem as the adhesive patch described by Raimondi (supra.) in that a large reservoir of lithium salt is needed, and in direct contact with skin, leading to a cumbersome patch that limits the duration of drug delivery related to practical volume restrictions. Moreover, these devices do not have control over the rate and/or quantity of Li delivered. These devices also require the use of an external battery, which further complicates their design and use.

SUMMARY OF THE INVENTION

The present invention provides new and novel methods and devices for administering lithium ions to a body component, for example across a tissue surface such as skin, a mucosal membrane, dura matter and the like, or directly into the bodily fluids of a mammal such as its blood plasma or cerebrospinal fluid (CSF) in a controllable and reproducible manner, and at the required rates to maintain a therapeutic level of lithium. The devices of the present invention are efficient, convenient, cost-effective, safe and reliable.

Thus, in one embodiment, this invention provides an iontophoresis device for the transdermal (or intradermal, or subcutaneous, or peritoneal) delivery (or for the delivery across any tissue surface, or for delivery to a biological fluid) of lithium ions, the device comprising a donor electrode that is a donor of a lithium ion; a protective architecture that is ionically conductive to the lithium ion, configured for application to a skin surface and positioned to isolate the donor electrode from the skin surface; and a counter electrode assembly configured for application to a skin surface, where the counter electrode assembly comprises a counter electrode operably coupled to the donor electrode. In various embodiments the donor electrode is selected from the group consisting of a lithium metal, a lithium alloy, and a lithium intercalation electrode. In certain embodiments the donor electrode comprises a lithium electrode, a lithium alloy electrode, or a lithium composite electrode. In certain embodiments the counter electrode assembly further comprises a sacrificial cathode that generally comprises a metallic salt in contact with a metal cathode. In certain embodiments the operable coupling comprises a galvanic couple formed by the donor electrode and the counter electrode. In various embodiments the galvanic couple generates an open circuit voltage of at least 2.0 V or at least 3.0 V. In certain embodiments the operable coupling comprises a switch and/or a resistor, and/or current or voltage regulation circuitry.

In certain embodiments the protective architecture is simply an impervious barrier layer that provides ionic transport for lithium ions produced by the donor electrode and is chemically stable to both the donor electrode anode and the biochemical environment of the skin surface. In certain embodiments the protective architecture is a fully solid-state composite composed of at least a solid interlayer that is chemically compatible with the donor electrode, and an impervious barrier layer that is chemically compatible with the biochemical environment of the skin surface. In certain embodiments the solid composite is a laminate composed of discrete layers. In certain embodiments the composite provides a graded transition between the layers. In certain embodiments the solid interlayer comprises a material selected from the group consisting of lithium nitrides, lithium phosphides, lithium halides, and lithium phosphorus oxynitride glass. In certain embodiments the solid interlayer of the protective architecture comprises a material selected from the group consisting of $Li_3N$, $Li_3P$ and LiI, LiBr, LiCl, LiF, and LiPON. In certain embodiments the impervious barrier layer of the protective architecture comprises a material selected from the group consisting of glassy or amorphous lithium ion conductors, ceramic lithium ion conductors, and glass-ceramic lithium ion conductors. In certain embodiments the barrier layer of the protective architecture comprises a lithium ion conductive glass-ceramic having the following composition:

| Composition | Mol % |
|---|---|
| $P_2O_5$ | 26-55% |
| $SiO_2$ | 0-15% |
| $GeO2 + TiO_2$ in which | 25-50% |
| $GeO_2$ | 0-50% |
| $TiO_2$ | 0-50% |
| $ZrO_2$ | 0-10% |
| $M_2O_3$ | 0 < 10% |
| $Al_2O_3$ | 0-15% |
| $Ga_2O_3$ | 0-15% |
| $Li_2O$ | 3-25% | and containing a predominant crystalline phase composed of $Li_{1+x}(M,Al,Ga)_x(Ge_{1-y}Ti_y)_{2-x}(PO_4)_3$ where $X \leq 0.8$ and $0 \leq Y \leq 1.0$, and where M is an element selected from the group consisting of Nd, Sm, Eu, Gd, Tb, Dy, Ho, Er, Tm and Yb and/or $Li_{1+x+y}Q_xTi_{2-x}Si_yP_{3-y}O_{12}$ where $0 < X \leq 0.4$ and $0 < Y \leq 0.6$, and where Q is Al or Ga.

In certain embodiments the protective architecture is a composite composed of an interlayer between a barrier layer and the donor electrode whereby the interlayer is impregnated with a non-aqueous anolyte, the anolyte interlayer being chemically compatible with and in contact with the donor electrode, and a barrier layer chemically compatible with the anolyte interlayer and with the biochemical environment of the skin surface and in contact with the anolyte interlayer. In certain embodiments the anolyte interlayer comprises a semi-permeable membrane impregnated with an anolyte composed of a non-aqueous lithium ion conducting liquid electrolyte. In certain embodiments the semi-permeable membrane is a micro-porous polymer. In certain embodiments the anolyte is in the liquid phase and comprises a solvent such as organic carbonates, ethers, esters, formates, lactones, sulfones, sulfolane and combinations thereof. In certain embodiments the anolyte comprises a solvent selected from the group consisting of EC, PC, DEC, DMC, EMC, THF, 2MeTHF, 1,2-DME or higher glymes, sufolane, methyl formate, methyl acetate, and combinations thereof and a supporting salt selected from the group consisting of $LiPF_6$, $LiBF_4$, $LiAsF_6$, $LiClO_4$, $LiSO_3CF_3$, $LiN(CF_3SO_2)_2$, and $LiN(SO_2C_2F_5)_2$. In certain embodiments the anolyte further comprises 1,3-dioxolane. In various embodiments the anolyte is in the gel phase. Various illustrative gel phase anolytes comprise a gelling agent selected from the group consisting of PVdF, PVdF-HFP copolymer, PAN, and PEO and mixtures thereof; a plasticizer selected from the group consisting of EC, PC, DEC, DMC, EMC, THF, 2MeTHF, 1,2-DME and mixtures thereof; and a Li salt selected from the group consisting of $LiPF_6$, $LiBF_4$, $LiAsF_6$, $LiClO_4$, $LiSO_3CF_3$, $LiN(CF_3SO_2)_2$ and $LiN(SO_2C_2F_5)_2$. In certain embodiments the impervious, lithium ion conductive, barrier layer comprises a material selected from the group consisting of glassy or amorphous lithium ion conductors, ceramic lithium ion conductors, and glass-ceramic lithium ion conductors. In certain embodiments the substantially impervious ionically conductive barrier layer is a lithium ion conductive glass-ceramic having the following composition:

| Composition | Mol % |
|---|---|
| $P_2O_5$ | 26-55% |
| $SiO_2$ | 0-15% |
| $GeO_2 + TiO_2$ in which | 25-50% |
| $GeO_2$ | 0-50% |
| $TiO_2$ | 0-50% |
| $ZrO_2$ | 0-10% |
| $M_2O_3$ | 0 < 10% |
| $Al_2O_3$ | 0-15% |
| $Ga_2O_3$ | 0-15% |
| $Li_2O$ | 3-25% | and containing a predominant crystalline phase composed of $Li_{1+x}(M,Al,Ga)_x(Ge_{1-y}Ti_y)_{2-x}(PO_4)_3$ where $X \leq 0.8$ and $0 \leq Y \leq 1.0$, and where M is an element selected from the group consisting of Nd, Sm, Eu, Gd, Tb, Dy, Ho, Er, Tm and Yb and/or $Li_{1+x+y}Q_xTi_{2-x}Si_yP_{3-y}O_{12}$ where $0 < X \leq 0.4$ and $0 < Y \leq 0.6$, and where Q is Al or Ga. In certain embodiments the impervious ionically conductive barrier layer has an ionic conductivity of at least $10^{-5}$ S/cm and/or the non-aqueous electrolyte separator layer has an ionic conductivity of at least $10^{-5}$ S/cm. In certain embodiments the donor electrode is a lithium or lithium alloy electrode; the counter electrode assembly comprises an Ag/AgCl electrode; and the protective architecture comprises a material selected from the group consisting of glassy or amorphous lithium ion conductors, ceramic lithium ion conductors, and glass-ceramic lithium ion conductors; and the operable coupling comprises a current regulator.

In various embodiments the device further comprises skin compatible conductive medium on the surface of the protective architecture that is to be applied to a skin surface. In certain embodiments the conductive medium comprises a conductive cream, lotion, ointment, gel, or paste. In certain embodiments the device can optionally further comprise a housing support structure made of a non-conductive material (e.g., a rigid or flexible polymer). The housing can optionally comprise a bio-compatible adhesive around the periphery of the device disposed for attachment of the device to a body or other tissue surface. In certain embodiments the device is encased in a biocompatible matrix or polymer compatible with implantation in a mammalian body and/or compatible with subcutaneous implantation.

Also provided are methods of administering lithium, to a mammal (e.g., a human, or a non-human mammal (e.g., feline, canine, equine, porcine, bovine, non-human primate, etc.) the method comprising applying a lithium delivery device as described herein to the skin (or other tissue) of the mammal, or implanting the device peritoneally or subdermally in the mammal, or using a penetrant device, whereby the device delivers the lithium to the mammal. In certain embodiments the mammal is a human (e.g., a human suffering from a psychiatric disorder).

Also provided are kits for the transdermal (or intradermal or intraperitoneal, or subdermal) delivery of a lithium ion to a subject (e.g. a human or other mammal in need thereof). In certain embodiments the kits comprise an iontophoresis device as described herein. In certain embodiments the kits further contain a skin compatible conductive medium (e.g., liquid, gel, paste, lotion, ointment, adhesive, etc.). In certain embodiments conductive medium is provided separate from the device, while in other embodiments, the conductive medium is on the surface of the protective architecture that is to be applied to a skin surface and/or on the counter electrode. In certain embodiments the kits further include instructional materials teaching the use of the device for the delivery of lithium to a mammal.

These and other features of the invention are further described and exemplified in the detailed description below.

BRIEF DESCRIPTION OF THE DRAWINGS

FIG. 5A illustrates a cross sectional depiction of an alternative arrangement of the electrodes of an electro-transport device 100 for delivery of lithium ions across a tissue surface 200, while FIG. 5B illustrates a top down view of the electro-transport device illustrated in FIG. 5A. As illustrated in the figure, the device comprises a protected anode (donor electrode) 110 comprising a lithium electrode 102, and a protective membrane 104. The device is illustrated with optional cathode electrolyte reservoir layers 122, and optional anode electrolyte reservoir layer 112. Also shown is the cathode 120 (e.g., silver chloride electrode) which in some embodiments also has a protective membrane architecture that can be the same or different than the protective membrane architecture of 104. The anode and cathode are operably coupled to each other via cathode terminal connector 128, optional electronic control unit 130, and anode terminal connector 108.

DETAILED DESCRIPTION

Figure 1:
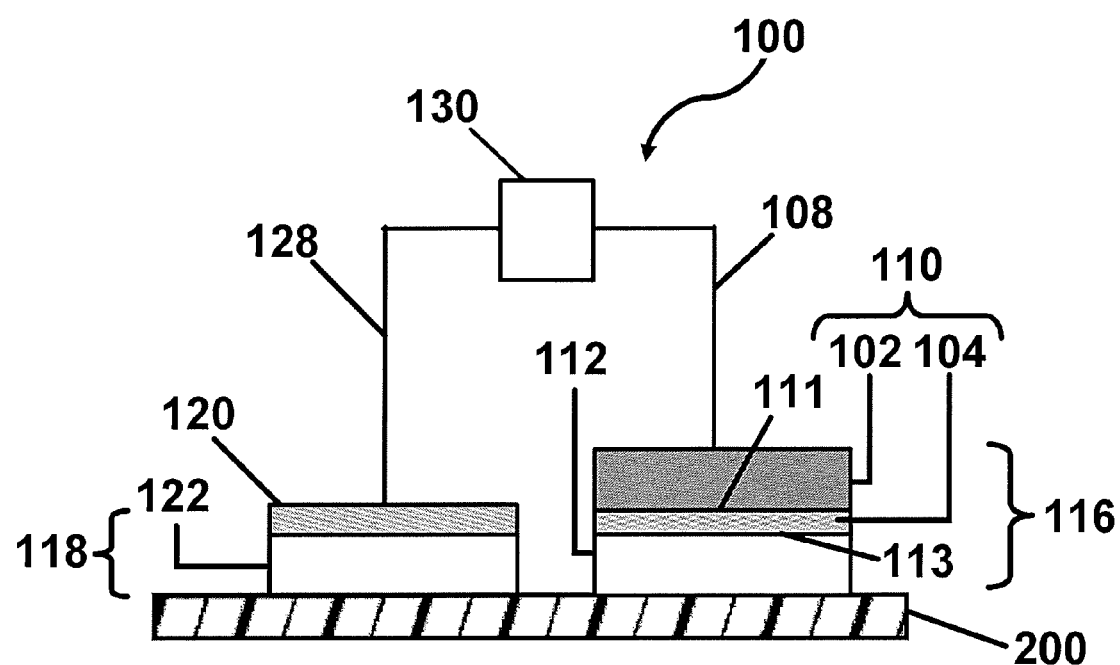
FIG. 1 schematically illustrates a cross sectional depiction of an electro-transport device 100 for delivery of lithium ions across a tissue surface 200. The figure illustrates the donor (lithium) electrode 102, and protective architecture 104, which together form a protected (lithium) anode 110, and optional anode electrolyte reservoir 112. Also shown is a counter electrode (cathode) 120 and optional cathode electrolyte reservoir 122, as well as a cathode terminal connector 128 and an anode terminal connector 108 connecting to an optional control unit 130.

The present invention provides new and novel devices and methods for administering lithium to a mammalian subject, especially the delivery of lithium (Li) ions to a body component for example across a body or tissue surface such as skin or a mucosal membrane, or for delivery of lithium ions directly to bodily fluids of a mammalian subject, such as its blood plasma or cerebrospinal fluid (CSF). The methods and devices of the present invention are efficient, convenient, safe and cost-effective.

Definitions

A "lithium electrode" refers to an electrode that can act as a source or donor of lithium ions. A "lithium electrode" includes, but is not limited to, lithium metal electrodes, lithium alloy electrodes, lithium intercalation electrodes, and the like.

The term "donor" when used with respect to an electrode (e.g., a lithium electrode) indicates that the electrode is a source of, i.e., produces or increases the availability of lithium ions, typically by a redox reaction such as electrochemical oxidation.

The term "operably coupled" or "operably connected" when used with reference to coupling of a donor electrode to a counter electrode indicates an electrical connection between one or more donor electrodes and one or more counter electrodes. The operable coupling can include simple electronically conductive contact, and/or can include formation of a galvanic couple between the donor and counter electrode(s) and/or can include optional control circuitry and/or optional switch, and/or optional power supply.

The term "ionic communication" when used with reference to ionic communication between a first material and a second material, such as between an electrode and a tissue or between an electrode and a body fluid or between different lithium ion conducting layers in a protective architecture (for instance, between a barrier layer and an interlayer) indicates that lithium ions can pass from the first material to the second material, for instance from the electrode into the tissue, although ionic communication may not require direct contact between the first and second materials, for instance the electrode and the tissue or body fluid.

By the term "chemically compatible" or "chemical compatibility" it is meant that the referenced material does not react in contact with another material to form a product that is deleterious to device operation.

Introduction

The lithium electro-transport (e.g., iontophoresis) devices of the instant invention comprise a lithium "donor" electrode that acts as a source of lithium ions intended for delivery to the mammalian subject. The donor electrode comprises an electroactive material comprising lithium (sometimes referred to herein as a lithium electroactive material or more simply as electroactive lithium) that upon electrochemical oxidation releases lithium ions for transport across the tissue surface and/or directly into a body fluid. The lithium electroactive material is generally a solid, such as lithium metal or a lithium alloy (e.g., lithium aluminum alloys, lithium silicon alloys, lithium tin alloys, lithium silver alloys), or a lithium intercalation host compound (e.g., $LiC_x$) containing lithium intended for electro-transport delivery to the subject. In a preferred embodiment the donor electrode is lithium metal; for instance, in the form of a lithium metal foil. Lithium electroactive materials in accordance with the present invention can be, and generally are, moisture sensitive, unstable in ambient air and corroded by aqueous media.

The electro-transport devices of this invention utilize a protective architecture, generally in the form of layer, which is disposed between the donor electrode and a body component of the mammal such as the surface of a tissue (e.g., skin, a mucosal membrane, dura matter and the like) or a bodily fluid. The protective architecture isolates the electrode from ambient air and the environment of or nearby the tissue surface and, when present, aqueous media, while allowing lithium ions to pass through the architecture for eventual transport to the mammal (e.g., across the tissue surface). Utilizing such a protective architecture, highly reactive and/or potentially toxic electrodes can thereby readily be incorporated in the devices of the present invention.

The protective architecture enables the use of a lithium donor electrode (e.g., an electrode fabricated from lithium metal or containing an intercalated lithium) as, for example, the anode of an electro-transport device for delivery of lithium ions across a body surface (e.g., skin).

The protective architecture comprises one or more components configured to provide a first architecture surface chemically compatible in contact with the lithium donor electrode, and a second architecture surface chemically compatible with the environment on the other side of the architecture, referred to herein as the "mammalian side" of the architecture, which may include ambient air, aqueous media and the biochemical environment of a tissue surface (e.g., skin surface, mucosal membrane, etc.). Generally the environment on the mammalian side of the architecture is a moisture rich, lithium anode corrosive, environment.

The architecture includes a lithium ion conductive impervious component comprising an impervious solid-state electrolyte material that is intrinsically conductive to lithium ions and chemically compatible with electroactive lithium corrosive environments from the mammalian side. The impervious solid-state electrolyte material is generally a ceramic, glass-ceramic or an inorganic glassy or amorphous material.

By intrinsically (or inherently) conductive it is meant that the material does not depend on the presence of a liquid, or a liquid electrolyte, or any other agent for its lithium ionically conductive properties.

In various embodiments, the impervious lithium ion conductive component of the protective architecture is a layer referred to herein as an impervious barrier layer or more simply a barrier layer. When used with reference to a barrier layer, by the term impervious it is meant that the layer provides a barrier that prevents fluids, into which it comes in contact during normal device operation and storage, from passing through the layer and transporting from one side of the layer to the other side. The barrier layer is also a lithium ion conductor which under the influence of an electrical field allows for the transport of lithium ions to pass through it, while at the same time remaining impervious to fluids.

In various embodiments, the lithium ion conductive impervious component (e.g., a barrier layer) is separated from the lithium anode by another lithium ion conducting component (e.g., an interlayer) that is in contact with the donor electrode and chemically compatible with electroactive lithium.

In some embodiments, the protective architecture is, or comprises, an ionically conductive protective composite, the composite comprising a first component (e.g., an interlayer as described herein) in contact with the anode, the first component comprising a material that is ionically conductive and chemically compatible with electroactive lithium; and a second component (e.g., a barrier layer as described herein) in contact with the first component material, the second component comprising a material that is impervious, inherently ionically conductive and chemically compatible with the first component material and electroactive lithium corrosive environments (i.e., an impervious solid-state electrolyte material as it is generally referred to herein). The protective composite may be laminate and/or graded. Ionically conductive protective composites suitable for use as, or as part of, a protective architecture in protected donor electrodes of this invention are fully described in commonly assigned U.S. patent application Ser. No. 10/772,157, filed Feb. 3, 2004; Ser. No. 10/825,587, filed Apr. 14, 2004; and Ser. No. 10/772,228, filed Feb. 3, 2004; incorporated by reference herein in their entirety and for all purposes.

In other embodiments the ionically conductive protective architecture on a first surface of the lithium anode comprises a lithium ion conducting separator layer comprising a non-aqueous anolyte (by anolyte it is meant, a lithium ion conducting liquid electrolyte about the anode), the separator layer being chemically compatible with electroactive lithium, and in contact with the anode, and an impervious ionically conductive layer (i.e., a barrier layer), comprising an impervious solid-state electrolyte material, chemically compatible with the separator layer and with aqueous environments, and in contact with the separator layer. This type of protective architecture is described in commonly assigned U.S. patent application Ser. No. 10/824,944, filed Apr. 14, 2004, incorporated by reference herein in its entirety and for all purposes. This type of protective architecture is sometimes referred to as an ionically conductive protective interlayer architecture, or a partially solid-state architecture. When incorporated in a protective architecture, the lithium ion conducting separator layer comprising non-aqueous anolyte, as described above, is sometimes referred to herein as an anolyte interlayer.

In certain embodiments, the protective architecture can simply be a barrier layer or the architecture can be an assemblage of various material layers disposed on either side of the barrier layer and having a layered arrangement that brings about the requisite properties of a protective architecture, including i) a fluid barrier that prevents electroactive lithium incompatible fluids that are present on the mammalian side of the architecture from contacting the donor electrode; ii) a conductor of lithium ions that, under the influence of an electrical field, allows lithium ions to pass through the architecture from the donor electrode to constituents on the mammalian side of the architecture (e.g., tissue, electrolyte reservoir, bodily fluids); and chemically compatible on one side in contact with the donor electrode and chemically compatible, on the other side (the mammalian side) with moisture rich environments including ambient air, biochemical environment of the tissue and aqueous media when present.

In various embodiments, the protective architecture comprises at least two layers: a barrier layer and an another lithium ion conducting layer, generally referred to herein as an interlayer, incorporated into the architecture to enhance its interface with the donor electrode and generally improve protected donor electrode properties. In certain embodiments, the interlayer is in direct contact with the barrier layer. Additional lithium ion conducting layers can be disposed between the interlayer and the barrier layer, such as a third, or fourth or more, lithium ion conducting layer(s). Generally, it is preferable to minimize the number of layers between the barrier layer and the interlayer in order to reduce complexity of the architecture. In certain embodiments the interlayer is solid-state, and generally referred to herein as a solid-interlayer. In alternative embodiments, the interlayer of the protective architecture may comprise an anolyte, which is a non-aqueous liquid electrolyte about the anode. An interlayer containing an anolyte is generally referred to herein as an anolyte-interlayer. For instance, an anolyte-interlayer can be a gel electrolyte, and/or a polymer swelled/plastisized/imbibed with anolyte, and/or a porous membrane (e.g., a microporous membrane) impregnated with anolyte. Protective architectures comprising a barrier layer and an anolyte-interlayer are sometimes referred to herein and elsewhere as a partially solid-state architecture.

Protective architectures having an impervious barrier layer and a solid-interlayer, and which are suitable for use in donor electrodes of the instant invention, are fully described in commonly assigned U.S. patent application Ser. No. 10/772,157, filed Feb. 3, 2004; Ser. No. 10/825,587, filed Apr. 14, 2004; and Ser. No. 10/772,228, filed Feb. 3, 2004, and which have already been incorporated herein by reference. In certain embodiments, the architectures described therein comprise an ionically conductive protective composite comprising a barrier layer (generally referred to therein as a second component layer) and a solid-interlayer (generally referred to therein as a first component layer).

Partially solid-state protective architectures comprising a barrier layer and an anolyte-interlayer are described in commonly assigned U.S. patent application Ser. No. 10/824,944, filed Apr. 14, 2004 and already incorporated by reference. In this reference, the barrier layer is generally referred to therein as an impervious lithium ion-conducting layer and the interlayer is sometimes referred to therein as a separator layer impregnated with anolyte.

The impervious lithium ion conductive component of the protective architecture is, generally, an impervious barrier layer. In various embodiments, the impervious barrier layer is fabricated as a freestanding layer, which can be incorporated into a partially solid-state protective architecture having an anolyte-interlayer disposed between it and the donor electrode or a fully solid-state protective architecture can be built-up from the freestanding barrier layer by sequential deposition of solid lithium ion conducting layers, including deposition of an interlayer followed by deposition of electroactive lithium (e.g., lithium metal).

The protective architecture chemically isolates the lithium donor electrode from the biochemical environment on the mammalian side while allowing facile transport of lithium ions for drug delivery. In accordance with the present invention, lithium donor electrodes having protective architectures are generally referred to as protected lithium anodes (or protected (lithium) donor electrodes, or more simply protected anodes). For instance, the use of protected anodes can allow the intimate contact of any lithium source with moisture rich environments, such as ambient air, and aqueous media (such as bodily fluids and aqueous solutions of the electrolyte reservoir)

In accordance with embodiments of the instant invention, protected donor electrodes comprise: a lithium anode having a first surface and a second surface; and a protective architecture on the first surface of the anode, the architecture having a first component (e.g., an interlayer) ionically conductive and chemically compatible with electroactive lithium on a side in contact with the lithium anode, and a second component (e.g., a barrier layer) that is impervious, ionically conductive and chemically compatible and in contact with constituents from the environment on the mammalian side, which generally are incompatible and/or corrosive if in contact with electroactive lithium; wherein the architecture comprises an impervious solid-state electrolyte material.

Thus, in various embodiments, the present invention pertains to a protected lithium donor electrode (i.e., a protected lithium anode) for use as an anode in an electro-transport device (e.g., an iontophoresis device). In typical embodiments, the protected anode is one of two or more electrodes that comprise an electro-transport delivery device. Commonly, at least a second electrode is provided which acts as a cathode.

In accordance with the present invention, the protected lithium anode when utilized in an electro-transport device acts as both a source of lithium to be delivered and as current distributing electrode that establishes an electric field that provides the driving force to assist in the electrical migration of Li ions through the protective architecture and across the tissue surface (e.g., skin). In one illustrative embodiment, the lithium electrode is metallic lithium and as such provides the most compact source of deliverable lithium. Li ions generated by electro-oxidation of the lithium metal anode can transport through the protective architecture under the influence of an electric field, and after passing through the architecture the Li ions can move across the tissue surface driven in part by electrical migration through the electric field. The electric field may be produced by an external power source, such as a battery, or it may be established by the potential difference between the lithium metal anode and the cathode.

Because of the highly reducing nature of lithium electrodes and by proper selection of a suitable cathode a significant galvanic potential difference can be established between the protected lithium anode and the cathode. As a result, in various embodiments, electro-transport devices of the instant invention can be self-powered, in that sufficient electro-motive force (EMF) is generated by the galvanic couple between the anode and cathode to drive the electrochemical redox reactions at the anode and at the cathode, and to actively drive the Li ion current through the protective architecture and across the tissue surface. In other embodiments, an external power supply (e.g., a self contained battery) is incorporated as part of the devices of the instant invention and the EMF provided by the galvanic couple between the lithium donor electrode and counter electrode can be used to augment the power needed to run the electro-transport device. In certain embodiments, the battery can be used simply to power microelectronics in a voltage and/or current regulating and/or sensing circuit, while the galvanic couple drives the ion transport.

Because electro-oxidation at the lithium anode only generates Li ions, the electro-transport devices of the instant invention have high efficiency of drug delivery, since extraneous ions (competitive ions) that would otherwise compete with Li ions for transfer across the tissue are not generated at the anode.

Protected lithium electrodes as used as anodes in electro-transport devices as described herein offer many advantages over systems where the source of lithium is a soluble salt and the anode current distribution electrode (typically a sacrificial Ag electrode) generates unwanted species in the form of competitive ions (e.g., Ag ions). The volumetric advantage of using lithium metal as a source of Li ions is at least a factor of 6 to about 15 over systems in which the source of lithium is a soluble salt such as lithium chloride, and much higher (e.g., about 300 times) for systems that utilize insoluble salts such as lithium carbonate. Furthermore, the improved efficiency of drug delivery, due to the fact that only Li ions are formed at the anode, means a lower current density across the tissue is required for a given drug delivery rate.

This can improve patient compliance and minimize certain potential side-effects. For instance, a patient can become sensitized to the application of an ionic current beyond a certain threshold value. The use of protected lithium anodes in devices according to the present invention offer an advantage in that a lower current density can be applied across the skin for a given drug delivery rate or the drug delivery rate can be increased while remaining below the threshold current density. Furthermore, drug delivery devices of the instant invention provide both a convenience and cost advantage in that the combination of the protected lithium anode and the cathode forms a galvanic couple that in certain embodiments allows operation of the device without the use of an external power supply and allows for a more compact, less cumbersome device.

Furthermore, because no extraneous ions are generated at the anode, there is no need to implement techniques to immobilize unwanted ions in order to increase efficiency, such as by precipitation. For instance, competitive Ag ions that are generated by oxidation of a Ag electrode can be immobilized by precipitation of a AgCl precipitate in order to improve efficiency of Ag electrodes for drug delivery. Precipitation methods (e.g., Ag ions to AgCl) suffer from the fact that they produce a precipitate that may impede performance over the course of delivery, and can eventually cause severe clogging of the electrodes. Since the donor electrodes of the present invention generate lithium ions intended for delivery, the devices of the instant invention do not suffer from this drawback, and enhanced efficiency can be achieved without precipitation—thereby avoiding clogging and of the electrode assembly.

The protected lithium anodes in accordance with their use in an electro-transport device of the instant invention also provide a significant safety factor in that a source of the lithium ions is removed from direct contact with the tissue surface by the protective architecture, which mechanically and chemically isolates the lithium electrode. For instance, when the device is stopped or if the integrity of the skin is compromised in anyway, unwanted delivery of Li ions through the compromised skin is mitigated by the presence of the protective architecture. This is in stark contrast to devices where a reservoir of highly concentrated dissolved lithium salt, or high concentration of the salt itself is in intimate contact with the skin. Furthermore, by using a protective architecture, the amount of lithium ions present in the anode electrolyte reservoir can be controlled, monitored and minimized, since lithium ions can only migrate through the architecture under an electric field, their transport from the donor electrode to the anode electrolyte reservoir can be precisely controlled and monitored by the electronic control unit of the device.

In another aspect, the present invention provides a method for administering therapeutic doses of lithium ions to a subject for treatment by electro-transport of the ion across a tissue surface such as skin. In certain embodiments the method generally involves electro-oxidation of the lithium donor electrode with concomitant release (liberation) of lithium ions for delivery across the tissue (e.g., the skin of a subject to be treated). Once released by electro-oxidation, the lithium ion moves across the protective architecture and becomes available for electro-transport by either or both passive and active delivery through the body surface. Passive delivery is generally based on diffusion driven by concentration gradients. In active delivery extrinsically applied driving forces such as an electrical potential assists in the migration of the ion through the body.

Generally, the delivery device of the instant invention operates by connecting the anode to the cathode through a precision resistor (or galvanostat), and as a result Li ions are liberated at the anode in proportion to the load resistance (or at a constant current in the case where a galvanostatic circuit is used), and therefore the concentration of lithium can be precisely controlled. Indeed, the lithium electrodes of the instant invention, in conjunction with any number of suitable counter electrodes (cathodes), gives rise to an electromotive force that can drive a Li ion current through the skin at suitable rates for Li uptake. For example, the open circuit EMF between a lithium metal electrode and a silver chloride counter electrode is about 3 volts. Accordingly, in a certain embodiment of the invention, an external electrical source, such as a battery, is not needed to drive the electrotransport current of the delivery device.

In various embodiments the present invention pertains to an electro-transport device for the delivery of lithium ions across a tissue surface (e.g., skin). The electro-transport device comprises a protected lithium anode and a cathode. In certain embodiments the device is self-powered in that the combination of the anode and the cathode forms a galvanic couple that provides the necessary electromotive force to drive electrochemical reduction at the cathode and oxidation at the anode and to drive the lithium metal ion, generated at the anode, across the body surface (e.g., skin) of a subject for treatment. In other embodiments, the device incorporates an external power supply, such as a battery, and as such the galvanic potential between the donor and counter electrodes can be used to augment or complement the power supplied by the battery in order to operate the device. In certain embodiments, the galvanic potential between the donor and counter electrodes is harnessed to drive the electrotransport current through the skin and external battery is used to power device electronics.

In use, the various devices described herein are placed in direct contact with a tissue surface (e.g., the skin surface of the body surface), such that the electrodes (anode and cathode) are both in ionic communication with the tissue, e.g., directly or through an electrolyte reservoir layer, which completes the electrical circuit through the tissue. By connecting the anode terminal to the cathode terminal, directly or through an electronic control unit (e.g., precision resistor, current or voltage regulator, etc.), electrons are driven by the EMF of the galvanic couple from the anode to the cathode, with concomitant release of a lithium ion from the protected lithium anode and generally into the tissue surface or into an anode electrolyte reservoir layer where the ion is then actively driven or passively diffuses across the tissue surface. In certain embodiments, the protected anode is metallic lithium having a protective architecture disposed on a major surface of the anode. The protective architecture is in lithium ion communication with the anode electrolyte reservoir layer or tissue surface on the side of the protective architecture opposite the lithium electrode; the architecture is also in lithium ion communication with the protected lithium metal anode.

In certain embodiments the devices described herein can be used for therapeutic treatment of a psychiatric illness, including acute mania and bipolar (manic/depressive) disorder. In various embodiments, the devices of the instant invention can be utilized to attain and/or maintain therapeutic levels of lithium in the blood. Clinical parameters, toxicology and pharmacokinetics of lithium treatment for manic depression and the like, and recommended dosing and treatment methods for iontophoretically delivering lithium ions across the skin are described in U.S. Pat. No. 6,375,990 to Nemeroff which is hereby incorporated by reference in its entirety.

In various embodiments, lithium electro-transport devices, such as those described herein, can be used in conjunction with oral dosing treatments (e.g., oral ingestion of a lithium salt such as $Li_2CO_3$ and the like) in order to achieve a therapeutic level of lithium in the blood, and/or maintain that level over the course of treatment in a particularly efficacious manner that avoids toxic concentrations of $Li^+$ in the blood and keeps the iontophoretic current at levels which do not cause local skin sensation. Lithium treatment is associated with a very narrow margin of safety, and oral dosing with lithium salts is infamous for its adverse drug effects and sharp variability of lithium concentrations in the blood as a function of time ("sawtooth pattern"). In certain embodiments of the instant invention, combining both oral and electro-transport dosing can optimize lithium treatment. By this expedient, the iontophoretic current density can be reduced to values well below that which causes localized sensation and/or pain while at the same time keeping the oral dose low enough to avoid reaching toxic lithium blood concentrations. For instance, $Li^+$ blood concentrations can be achieved and maintained within the therapeutic window by properly synchronizing and tuning the iontophoretic delivery of lithium in accordance with the oral dosing and pharmacokinetics of the oral ingestion.

In various embodiments, the protective architecture comprises an impervious, lithium ion-conducting barrier layer comprising a ceramic or glass ceramic solid-state electrolyte material intrinsically conductive to lithium ions and having the following general stoichiometry: $Li_{1+x+y}(Al,Ga)_x(Ti,Ge)_{2-x}Si_yP_{3-y}O_{12}$ where $0.1 \leq x \leq 1$ and $0.1 \leq y \leq 1$. In certain embodiments, the protective architecture further comprises a lithium ion conducting interlayer in contact and disposed between the barrier layer and the donor electrode, the interlayer selected for its chemical compatibility with the donor electrode and the barrier layer. In certain embodiments the interlayer is solid and comprises a solid, inorganic, lithium single ion conducting glass such as LiPON, in other embodiments the solid interlayer is the product of a reaction between the lithium anode and a precursor material, such as $Cu_3N$ or red phosphorous which can be coated onto the surface of the barrier layer and then reacted with lithium to form a reaction product that is chemically compatible with the anode and conductive to lithium ions. In certain embodiments the interlayer comprises a lithium ion conducting anolyte (non-aqueous liquid electrolyte about the anode), generally organic. In accordance with this embodiment, the anolyte of the interlayer can be impregnated into the pores of a microporous separator or incorporated in a polymeric gel or swelled into a polymer component. In certain embodiments, the anode electrolyte reservoir layer, when present, comprises a hydrogel comprising an aqueous solution of supporting electrolyte salt (e.g., LiCl). In certain embodiments, the cathode is a silver chloride electrode in direct ionic communication with the tissue surface, or with a cathode electrolyte reservoir layer in contact with the tissue surface (e.g., body surface). In certain embodiments the electronic control unit connected to the terminal connectors of the anode and the cathode comprises a fixed or variable precision resistor, and/or a voltage regulator, and/or a current regulator.

The methods and devices of the present invention provide a number of advantages for the delivery of lithium metal ions across a body surface. First, the methods and devices afford high efficiency of drug delivery. The efficiency of lithium drug delivery may be defined as the number of moles of lithium ions that are delivered to the tissue (or the body) per faraday transferred from the anode to the cathode. Efficient drug delivery systems require lower current density and less energy to maintain a given drug delivery rate. For a system that is 100% efficient and has zero passive diffusion, the lithium ion drug delivery rate is equal to the current being run or drawn through the delivery device. In accordance with the present invention, the lithium delivery devices of the instant invention provide improved efficiency and do not require methods to minimize the effect of competitive ions formed at the anode, because the anodes of the instant invention only generate the lithium metal ion intended for delivery. This is in stark contrast to electro-transport drug delivery devices that use either polarizing (inert) anodes that hydrolyze water creating unwanted pH changes and competing protons or so called sacrificial anodes (e.g., silver chloride) that generate unwanted species that are generally highly mobile (e.g., Ag ions) and compete with the Li ion to be delivered, and as such require methods to minimize competitive ion effects, such as precipitation.

A second major advantage of the devices described herein is derived from the barrier properties of the protective architecture. Because of the imperviousness of the barrier layer, the architecture enables the use of a broad range of electroactive lithium materials in the donor electrode assemblies of the instant invention that would otherwise be unsuitable due to their incompatibility with ambient air, the tissue surface or, when present, the reservoir, which tends to be aqueous. For instance lithium metal, lithium alloys or compounds incorporating lithium with a potential near that (e.g., within about a volt) of lithium metal, are generally very reactive to moisture, aqueous and are certainly not biocompatible. The use of lithium electroactive materials that do not occur freely in nature and are reactive in ambient air, and corroded in aqueous media are enabled herein by the inventive donor electrode assemblies of the present invention for their use as an electrochemically active source of lithium in a protected lithium donor electrode.

A third major advantage is that the devices described herein can be self-powered. The protected lithium anodes used in the electro-transport devices of the present invention can form a galvanic couple with the cathode (e.g., a silver chloride electrode), and provide sufficient EMF such that the devices are self-powered and do not require an additional power source. This is in contrast to devices that require an external battery connected to both electrodes, which is both volumetrically cumbersome and very cost inefficient. In such devices either the battery is thrown away each time the ion source runs out, or a means of replacing the electrodes is required so that the battery can be continuously used until the battery is used up. This may cause another complication in that the battery may run out of power unbeknownst to the patient. In the self-powered devices of the present invention, power is generated by the galvanic couple between the anode and the cathode, so there is no chance that the device will run out of power before the required dosage has been delivered, especially where the device is designed to be anode limited.

A fourth major advantage is that the devices described herein are inherently safer in use than other delivery systems. The protective architecture provides an additional safety measure in that the source of the lithium ion is not in direct contact with the body so unwanted passive diffusion is minimized, particularly in the case of a skin breach. Furthermore, by this expedient, the devices of the instant invention can be configured for direct delivery to bodily fluids, and/or as an implantable device, and/or configured for subcutaneous delivery, since the source of lithium is isolated by the protective architecture, lithium ions are liberated from the donor electrode and made available for delivery only by controlled electrochemical oxidation.

Additionally, devices described herein can be intrinsically more compact. Since, in various embodiments, the source of the lithium ions to be delivered is the electrochemically active material (also known as the electroactive material) of the anode, the source can be provided in its most compact form, as metallic lithium.

The devices described herein also afford improved control over the rate of lithium ion delivery. Since the lithium electrode is the source of lithium ions, the present invention provides a method for precise and extremely accurate control and monitoring over the rate and quantity of Li ions transferred to the patient.

Illustrative Embodiments

The invention is now described with reference to a schematic illustration of a lithium electrotransport delivery device according to one embodiment of the present invention, as it would be used for transdermal delivery of lithium ions across the skin 200 of a subject to be treated by lithium for therapeutic or otherwise beneficial use. Referring to FIG. 1, an electro-transport device 100 is schematically depicted. The device illustrated therein comprises two electrodes, a lithium "donor" electrode 102 as anode and an "indifferent" electrode as cathode 120. The indifferent electrode is also referred to as a counter electrode and functions to complete the electrical circuit of the electro-transport device. The lithium donor electrode 102 can be "protected" with a protective architecture 104 thereby forming a protected lithium donor electrode 110.

Figure 2A:
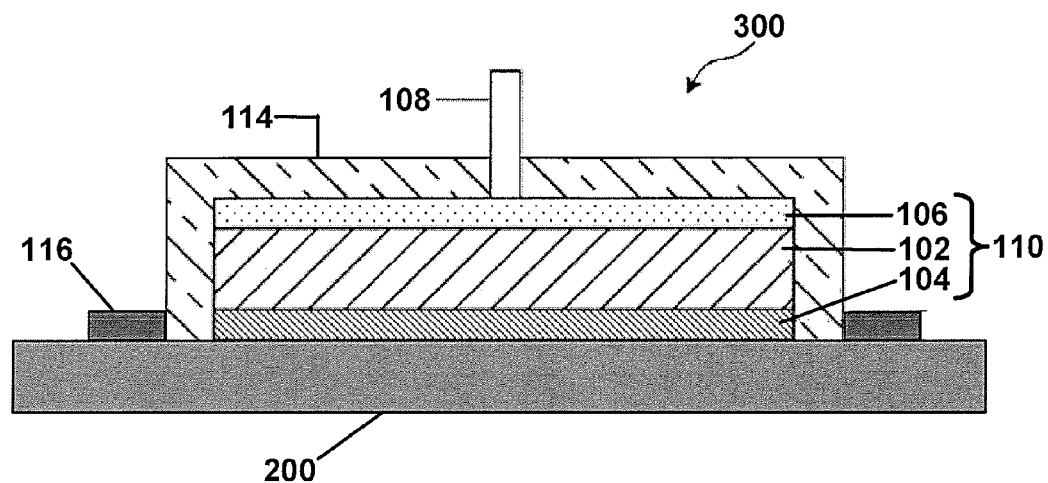
FIG. 2A schematically illustrates a cross sectional depiction of a protected lithium electrode (anode) dermal patch where the protected lithium electrode is contacted with the tissue surface, while FIG. 2B schematically illustrates a cross sectional depiction of a protected lithium electrode (anode) dermal patch where a reservoir is disposed between the protected lithium electrode and the tissue surface. The device comprises an anode housing support structure 114 (e.g., flexible polymer), and can be attached to a tissue surface 200 using, e.g., a biocompatible pressure sensitive adhesive. The lithium electrode 102 is shown with the protective membrane architecture 104, and an optional current collector 106 (e.g. conducting foil such as copper foil) that together form a protected anode 110. The anode can be operably connected to a cathode via the anode terminal connector 108.

It is contemplated in certain embodiments that the protective architecture 104 of the protected anode 110 is placed in intimate contact with the skin 200 (see, e.g., FIG. 2A). In various other embodiments, however, an anode electrolyte reservoir layer 112 is disposed between the skin and the anode (see, e.g., FIG. 2B). The lithium electrode 102, protective architecture 104 and optional reservoir 112 together form a "donor" electrode assembly 116. When present, the anode electrolyte reservoir layer generally contains a biocompatible material, such as, for example, a water absorbent hydrophilic polymer (e.g., a gelling polymer such as a hydrogel) that is water swellable and is absorbed with an electrolyte solution or a porous material such that the electrolyte solution is retained inside its pore structure. Suitable hydrophilic polymers include, but are not limited to POLYOX®, cellulose, cellulose derivatives (e.g., methyl cellulose, etc.), and the like. Further examples of suitable water swellable polymers are described in U.S. Pat. Nos. 5,405,317 and 5,162,042, which are incorporated herein by reference. In various embodiments the electrolyte, when present, comprises an aqueous solution of a biocompatible supporting electrolyte salt (e.g., tetrabutylammonium chloride, or lithium chloride). When present, the anode electrolyte reservoir layer (e.g., an aqueous gel electrolyte) is sufficiently conductive to the lithium ions to facilitate their transport at the desired rate of ion drug delivery to the subject being treated.

In various embodiments, the cathode 120 is chosen such that in combination with the protected lithium anode 110 a galvanic couple is formed that is able to drive the electrochemical oxidation and reduction reactions at the anode and the cathode respectively, and provide an electromotive driving force that assists in the electrical migration of the Li ion across the skin. For instance, the potential difference between a lithium metal electrode and a silver chloride cathode is, in accordance with the following electrochemical reaction, 3.27 V:

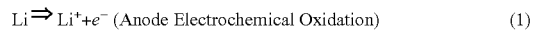

$$\text{Li} \Rightarrow \text{Li}^+ + e^- \text{ (Anode Electrochemical Oxidation)} \quad (1)$$

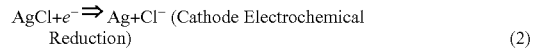

$$\text{AgCl} + e^- \Rightarrow \text{Ag} + \text{Cl}^- \text{ (Cathode Electrochemical Reduction)} \quad (2)$$

In certain embodiments the counter electrode can optionally an electrolyte reservoir layer 122 disposed between the tissue surface 200 and the cathode 120. The cathode and optional electrolyte reservoir layer together form a counter or indifferent electrode assembly 118. The electrolyte reservoir layers, when present, facilitate ionic transport communication while providing a physical separation between the respective electrodes and the tissue surface 200. An insulator such as an air gap or insulating material (e.g., a non-conducting or low conductivity polymer), not shown in FIG. 1, can be used to separate the anode and cathode reservoir layers. Insulating, non-swelling, polymeric materials that are useful to provide the gap are known to those of skill in the art of electro-transport drug delivery. Such materials include, but are not limited to ethylene vinyl acetate, polyethylene and polypropylene. Typically, both the anode and the cathode comprise electronically conducting terminals and/or current collectors that facilitate electronic communication (electronic current flow) between the anode and the cathode. The anode terminal 108 and cathode terminal 128 may be directly shorted to each other, but are more typically connected to an electronic control unit 130, such as a precision resistor, galvanostat, voltage and/or current sensor or regulator, and the like.

In certain embodiments the donor electrode can have a large negative potential versus the standard hydrogen electrode (vs. SHE). For instance lithium metal has a potential of −3.04 V vs. SHE. Lithium electroactive materials that are within about 2 volts positive of the lithium potential (e.g., between about −1 V to −3 V vs. SHE) are generally very reactive and react in contact with water of an aqueous solution and moisture from the air. In accordance with this invention, the protective architectures enables the use of lithium electroactive materials in donor electrodes having a potential vs. SHE that is more negative than the reduction potential of water. For instance the electrochemical potential of lithium electroactive materials that can be used in a protected donor electrode of the instant invention can be more negative than −1 V vs. SHE, or more negative than about −2V vs. SHE, or more negative than about −2.5 V vs. SHE.

The use of electroactive lithium in a protected donor electrode having a potential that is more negative than the reduction potential of water allows for the devices of the instant invention to have voltages that are larger than the thermodynamic voltage stability window of water, which is 1.23 V. As such, in certain embodiments the devices of the instant invention can generate an open circuit potential between the donor and counter electrode that is greater than 1.23 V. In certain embodiments, the open circuit voltage difference between the donor and counter electrodes of the devices of the instant invention are greater than about 2V, and can be greater than about 3V or higher. For instance, the electrochemical open circuit potential between a protected lithium metal donor electrode and Ag/AgCl cathode is 3.27V.

Furthermore, while schematic illustration of FIG. 1 shows only a single donor electrode and a single counter electrode, embodiments comprising multiple donor electrodes and/or multiple counter electrodes as well as their associated electrode assemblies are also contemplated.

Donor Electrode

The donor electrodes of the instant invention are so-called because they are a source (i.e., a donator) of lithium ions intended for drug delivery, and the lithium supply is stored in the donor electrode as or as a constituent of an electroactive material. During device operation, electrochemical oxidation of the electroactive material leads to a concomitant release of lithium ions from the donor electrode, which thereby facilitates lithium drug delivery. Accordingly, the donor electrodes of the instant invention are an electrochemically active source of deliverable lithium. Generally, the electroactive material is a solid. In various embodiments, the electroactive material is moisture sensitive and reactive in moisture rich environments such as ambient air and the biochemical environment of tissue, and/or aqueous media such as aqueous solutions of the electrolyte reservoir or bodily fluids.

Examples of suitable lithium electroactive component materials include, but are not limited to, lithium metal, lithium alloys and lithium intercalation compounds, especially lithium metal since it is the most compact and simplest electroactive source of lithium. Binary and ternary lithium alloys with Ca, Mg, Sn, Ag, Zn, Bi, Al, Cd, Ga, In. Specific examples of preferred lithium alloys include lithium aluminum alloys, lithium silicon alloys, lithium tin alloys, lithium silver alloys. Lithium electrodes, including lithium metal, lithium alloy and lithium intercalation are well known to those of skill in the art of lithium batteries.

The amp-hour capacity of the donor electrode should be sufficient to support its function as a source of deliverable lithium. In various embodiments, the donor electrode is lithium metal. In certain embodiments the lithium metal donor electrode is in the form of a layer (e.g., a lithium metal foil) of sufficient thickness to support its function as a source of deliverable lithium. The gravimetric capacity of lithium is 3.86 Ah/gr, and its density is about 0.53 g/cc. Accordingly, 5 microns of lithium supplies a capacity of 1 mAh/cm². In order to deliver 50 mg of lithium from a donor electrode having an active area of about 10 cm², the lithium foil thickness required is about 95 microns. For an electrotransport device of the instant invention to operate for 10 days supplying about 50 mg of lithium per day a foil thickness of about 1 mm is required, for one month of delivery at that daily rate, the lithium foil thickness would need to be about 3 mm thick. Because the donor electrodes of the instant are protected from the ambient environment, and by the fact that lithium ions is generated by the donor electrode thus circumventing associated competitive ion precipitation impediments, the protected donor electrodes of this invention can be utilized to deliver lithium to a patient over extended periods. For instance, in certain embodiments the devices may contain a protected donor electrode having a sufficient source of lithium to deliver that lithium to a patient for a period of at least one week, preferably about a month or longer, more preferably several months (e.g., 3 months). In certain embodiments, the devices of the instant invention can be loaded with enough lithium in the protected donor electrode for extended use for up to 1 year. In various embodiments of the devices of the instant invention, once the source of lithium in the protected donor electrode runs out, it can be replaced with a new protected donor electrode within the original electrotransport device housing.

While in some embodiments, direct electronic contact can be made between the lithium anode and the anode terminal connector, it is more common to affix a current collector to the back of the lithium electrode in order to facilitate uniform current collection and to make electrical contact between the current collector and the anode terminal. Suitable current collectors for lithium electrodes are known to those of skill in the art of lithium batteries, and these include, but are not limited to, copper foil and Ni mesh.

In certain embodiments, the electroactive material comprises an intercalation compound. Intercalation/de-intercalation reactions involve the insertion/removal of a guest species (the intercalant) into/out-of an intercalation host compound. Generally, in the case of a lithium intercalation compound, electrochemical reduction leads to insertion of lithium ions into the host, with removal of lithium ions out of the host upon electrochemical oxidation. Intercalation compounds are well known in the field of lithium ion batteries, of which almost all such batteries comprise intercalation electrodes as both anode and cathode. During battery discharge, lithium ions shuttle from the anode to the cathode and then back to the anode during charge. Accordingly, lithium intercalation compounds are suitable as an electroactive material in lithium donor electrodes of the instant invention since they are able to store and then electrochemically release lithium ions by electro-oxidation.

The electrode reaction occurring at a lithium donor intercalation electrode can be described as follows, whereby Host is the intercalation compound and Li ions are the intercalant. Li ions are released as the host is electro-oxidized.

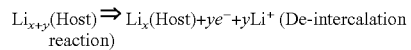

$$Li_{x+y}(Host) \Rightarrow Li_x(Host) + ye^- + yLi^+ \text{ (De-intercalation reaction)}$$

Intercalation compounds suitable for use as the electroactive material include, but are not limited to, lithium metal chalcogenides (e.g., oxides), lithium metal phosphates, and lithium metal silicates—especially, lithium transition metal oxides, phosphates and silicates. Specific examples include $LiNiO_2$, $Li_4Ti_5O_{12}$, $LiMn_2O_4$, $LiCoO_2$, $LiNi_xCo_{1-x}O_2$, $LiFePO_4$, $LiFe_3(PO_4)_3$, $LiC_6$, $LiWO_2$ and $LiMoO_2$. The chemical stability of these compounds generally changes depending on its state of discharge. For instance, $LiCoO_2$ and $LiFePO_4$ show reasonable stability and can be fabricated in ambient air. However, in the course of being oxidized, i.e., de-intercalation of lithium, the materials generally become very moisture sensitive and reactive in ambient and aqueous media.

In various embodiments the donor electrode(s) is simply, or essentially consists of, the electroactive lithium component; in other words, no other component besides the electroactive lithium component is needed for the electrode to properly function. Suitable examples include, but are not limited to, lithium metal and lithium metal alloys in a metal foil or metal sinter construct. Others include lithium intercalation electrodes wherein the intercalation material has sufficiently high electronic and lithium ion conductivity to support the electrical current flowing through the electrode.

In various embodiments the lithium donor electrode is a multi-component arrangement, comprising not only an electroactive component material, but also a lithium ion conducting component ("ionic-component") and an electronically conducting component ("electronic-component") intended to provide or enhance lithium ion or electron conductivity throughout the electrode, respectively. A binder component is also generally added to the electrode to effect intimate contact between the various components and provide mechanical integrity. Examples of suitable binder materials include polytetrafluoroethylene (PTFE), polyvinylidene difluoride (PVdF) and polyethylene oxide (PEO). Examples of suitable electronic components include carbons such as graphite and high surface area carbon blacks. The ionic component can be a liquid, gel and/or polymer electrolyte having lithium ion conductivity and chosen for its chemical compatibilty with the various other components of the electrode, particularly with that of the electroactive component(s). For instance, only non-aqueous electrolytes can be used as an ionic component in donor electrodes that are unstable in contact with water.

Typically, but not necessarily, intercalation electrodes are fabricated by coating a slurry comprising an electroactive component, a binder and a high surface area carbon onto a current collector, such as a copper, nickel, aluminum or stainless steel foil chosen, in part, based on its compatibility with the electroactive component. When incorporated into a battery, the pre-fabricated coated electrodes are placed in an appropriate package (e.g., a pouch or a can) along with other battery components, and a lithium ion conducting liquid electrolyte is added which in turn fills the pores of the electrode and functions to provide or enhance lithium ion conductivity throughout the electrode (see, e.g., U.S. Pat. Nos. 4,302,518; 5,616,309; 7,026,072; 5,334,334; and 5,595,837 which are incorporated herein by reference for all purposes).

Accordingly, in certain embodiments of protected donor electrodes, especially lithium intercalation electrodes having a multi-component arrangement that comprises a liquid ionic component (i.e., a liquid electrolyte), the electrode is generally pre-fabricated, e.g., as described above for batteries—without the liquid electrolyte component—and then during fabrication of the protected donor electrode, the pre-fabricated electrode is imbibed with a non-aqueous liquid electrolyte, for example by dispensing the electrolyte from a syringe, therein providing or enhancing its ionic conductivity.

Liquid electrolytes suitable for use as an ionic component in a donor electrode generally comprise a non-aqueous solvent and a supporting electrolyte salt. For example, the liquid electrolyte may include a solvent selected from the group consisting of organic carbonates, ethers, lactones, sulfones, etc, and combinations thereof, such as EC, PC, DEC, DMC, EMC, 1,2-DME or higher glymes, THF, 2MeTHF, sulfolane, and combinations thereof. 1,3-dioxolane can also be used as a solvent. Alternatively, the ionic component may be a gel electrolyte or it can be an electrolyte in the gel phase, gelling agents such as polyvinylidine fluoride (PVdF) compounds, hexafluoropropylene-vinylidene fluoride copolymers (PVdf-HFP), polyacrylonitrile compounds, cross-linked polyether compounds, polyalkylene oxide compounds, polyethylene oxide compounds, and combinations and the like can be added to gel the solvents. Suitable electrolytes will, of course, also include active metal salts, for example, $LiPF_6$, $LiBF_4$, $LiAsF_6$, $LiSO_3CF_3$ or $LiN(SO_2C_2F_5)_2$. The salt concentration of the electrolyte solution is commonly selected based on optimizing the lithium ion conductivity; generally, the concentration is in the range of about 0.2 molar to 1.5 molar, most commonly about 1 molar.

Protective Architecture

Generally, the lithium donor electrodes of this invention are highly reactive, moisture sensitive and, ergo, unstable and can degrade or even corrode, in contact with or in the proximity of moisture rich environments such as ambient air (e.g., oxygen and moisture) or the bio-chemical environment of tissue (e.g., skin) or aqueous media (e.g., from the electrolyte reservoir). In accordance with the present invention, a lithium ion conductive protective architecture is configured on the first surface of the anode to protect the donor electrode from any such degradation or corrosion by effectively shielding/isolating the anode from contact with any anode degrading or corroding fluids. In various embodiments, the donor electrode in combination with the protective architecture can form a protected donor electrode that is stable when exposed to ambient air and/or the biochemical environment of tissue, and/or in contact with tissue, and/or in contact with bodily fluids, and/or in contact with aqueous media of the anode reservoir.

Figure 2B:
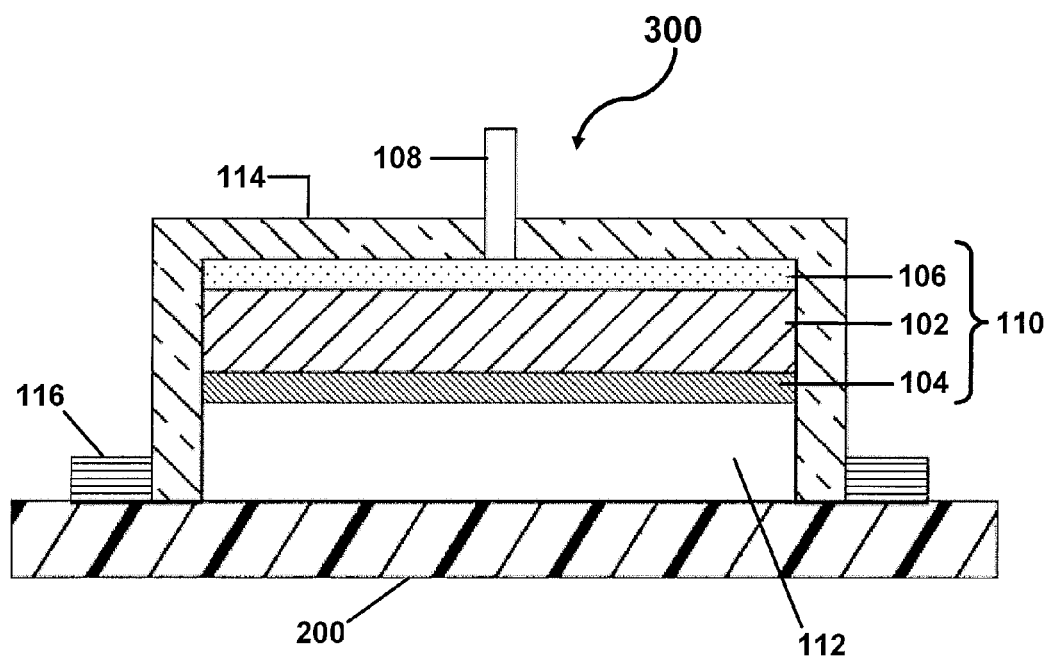
FIG. 2B depicts the optional reservoir 112, which is absent in FIG. 2A.

Referring back to the electrotransport device in FIG. 1, the protective architecture 104 is positioned on and in contact with a first surface of the donor electrode 102, and disposed between the donor electrode and the tissue surface 200 or, where present, the reservoir 112. The architecture, generally in the form of a layer, can be described as having a first 111 and second face 113. When properly positioned to isolate the donor electrode, the first face of the architecture is adjacent to, in contact with, and generally covers the first surface of the donor electrode 102. The second face 113 is adjacent to and in the proximity of, or in contact with, ambient air, and/or bodily component/fluid (e.g., tissue) and/or the anode electrolyte reservoir. In one embodiment of the electrotransport device, as it is shown in FIG. 2A, the second face of the architecture is in contact and generally aligned with the anode reservoir. In another embodiment, as shown in FIG. 2B, the architecture is in contact with tissue (e.g., skin).

During normal device operation and storage, the architecture provides a barrier against the transmission of anode corrosive/incompatible fluids, that might be and generally are, present in the environment on the mammalian side of the architecture—preventing any such fluids from contacting the donor electrode, while simultaneously allowing transport of lithium ions to pass from the donor electrode through the architecture under the influence of an electrical field. By this expedient, and in accordance with the instant invention, the architecture enables the use of highly reactive donor electrodes and facilitates the transfer of lithium from these electrodes to a mammalian subject intended for treatment.

Generally, the first and second faces of the architecture are exposed to different chemical environments, so their respective surfaces have different chemical compatibility requirements. The surface of the first face is chemically compatible in contact with the donor electrode, and in certain embodiments this means that the first face must be chemically compatible in contact with highly reactive metal lithium and the like. Whereas the surface of the second face is chemically compatible in contact with the environment on the mammalian side, generally anode corrosive, moisture rich, and/or aqueous media. In order to achieve chemical compatibility and/or optimize interfacial properties, the first and second faces of the protective architecture are, generally, composed of different material compositions.

A protective architecture in accordance with the instant invention: 1) conducts lithium ions and allows lithium ions to pass through the architecture (via electrical migration), thereby facilitating the transfer of lithium from the donor electrode to the tissue surface and/or to the anode electrolyte reservoir, when present; 2) provides a barrier against the transmission of anode corrosive/incompatible fluids from the ambient air, and/or tissue environment, and/or bodily fluids, and/or aqueous media, preventing such fluids from passing through the architecture and contacting the donor electrode; and 3) has a first face chemically compatible in contact with the lithium donor electrode and a second face chemically compatible with constituents it contacts on the mammalian side of the architecture, including moisture and/or water and/or aqueous media and/or bodily fluids.

In order to meet these requisites, the protective architecture comprises an impervious lithium ion-conducting component that is in contact with anode incompatible/corrosive fluids on the mammalian side of the architecture. In various embodiments, the impervious component of the architecture is in the form of an impervious barrier layer, which imparts its barrier properties to the architecture. Accordingly, the barrier layer provides an impervious barrier to fluids it contacts during normal device operation and storage, particularly anode corrosive fluids (e.g., ambient air, water, constituents of the tissue environment and aqueous media from the mammalian side), as well as other fluids such as non-aqueous liquid electrolytes that might be present in an anolyte interlayer or as an ionic component of a donor electrode, and thus may be in contact with the barrier layer. Generally, the barrier layer is impervious to all fluids it contacts during normal device operation and storage in order to facilitate hermetic isolation of the protected donor electrode. In accordance with the present invention, the barrier layer has no through porosity and does not allow fluids it contacts to permeate, flow, seep or otherwise pass through the layer. At the same time, the barrier layer is a lithium ion conductor that does allow lithium ions to pass through it under an electric field. In order to achieve these aims, the barrier layer comprises at least one impervious solid-state electrolyte material that is intrinsically conductive to lithium ions, impervious to fluids and does not swell or absorb liquids it contacts during normal device operation and storage, and chemically compatible with anode incompatible/corrosive fluids that it contacts and which are on the mammalian side of the architecture. By intrinsically (or inherently) conductive it is meant that impervious solid-state electrolyte material does not require a liquid, or for that matter a gel phase, or any other agent to facilitate or bring about Li-ion conduction or transport.

In various embodiments, the solid-state electrolyte material of the barrier layer is an inorganic lithium ion conductor chemically compatible and impervious in contact with moisture rich environments such as ambient air, and aqueous media. The inorganic solid-state electrolyte material of the barrier layer can be an amorphous or glassy material, a ceramic and a glass-ceramic consistent with the principles of a solid-state electrolyte material as described above. In some preferred embodiments the inorganic solid-state electrolyte material is a ceramic or a glass-ceramic. Because the solid-state electrolyte material contacts the environment on the mammalian side of the architecture, it is generally not a lithium ion-conducting polymer, since such polymers are usually very hydroscopic in ambient air and readily swelled by or take up water.

In accordance with the instant invention, the impervious solid-state electrolyte material is generally a ceramic, glass-ceramic or an inorganic glassy or amorphous lithium ion conductor. Moreover, it can be either or both a single lithium ion conductor and/or a highly selective lithium ion conductor (e.g., showing at least one, preferably at least two, more preferably at least three or four or more orders of magnitude greater conductivity for lithium than for other ions). Mixed electronic/ionic conductors are also contemplated.

Suitable solid-state electrolyte materials include, but are not limited to inorganic glassy or amorphous lithium ion conductors, such as, but not limited to lithium ion conducting silicate glasses having appropriate modifiers and network formers Suitable ceramic and glass-ceramic solid-state electrolyte materials include lithium metal phosphates such as those of the nasicon type (e.g., $Li_{1.3}Ti_{1.7}Al_{0.3}(PO_4)_3$) and the like. Suitable ceramic solid-state electrolyte materials include lithium metal oxides such as those of the perovskite type (e.g., $(Li,La)TiO_3$ and those of the garnet type (e.g., $Li_5La_3M_2O_{12}$ (M=Nb, Ta), and lithium beta alumina; and the like.

For instance, ceramics and glass-ceramics suitable as a solid-state electrolyte material include lithium metal phosphates such as lithium titanium phosphates, lithium germanium phosphates and lithium hafnium phosphates and combinations thereof, and for example prepared by processes such as, but not limited to, calcination and melt/quenching. For instance those of the type $LiM_2(PO_4)_3$, M=Ge, Ti, Sn, Hf, Zr, and the like. For example $Li_{1+x}M_x(Ti, Ge, Hf)_{2-x}(PO_4)_3$ where M is an element selected from the group consisting of Fe, Ga, Al and rare earth elements and where $0.1 \leq x \leq 1.9$; such as, for example where x is about 0.3. For example, $Li_{1+x+y}(Al,Ga)_x(Ti, Ge, Hf)_{2-x}Si_yP_{3-y}O_{12}$ where $0.1 \leq x \leq 1$ and $0.1 \leq y \leq 1$; such as, $Li_{1+x+y}(Al,Ga)_x(Ti, Ge)_{2-x}Si_yP_{3-y}O_{12}$ where $0.1 \leq x \leq 1$ and $0.1 \leq y \leq 1$; and $Li_{1+x+y}Al_xTi_{2-x}Si_yP_{3-y}O_{12}$ where $0.1 \leq x \leq 1$ and $0.1 \leq y \leq 1$. For example, $Li_{1+x+y}Al_xTi_{2-x}Si_yP_{3-y}O_{12}$ where $0.1 \leq x \leq 0.3$ and $0.1 \leq y \leq 0.4$ shows excellent conductivity.

Other specific examples of ceramics and glass-ceramics suitable as a solid-state electrolyte material include $Li_{0.3}La_{0.5}TiO_3$, $Li_2O.11Al_2O_3$, $Li_5La_3Ta_2O_{12}$, $Li_5La_3Nb_2O_{12}$, $Li_5TiP_3O_{12}$, $Li_3Fe_2P_3O_{12}$, $Li_4NbP_3O_{12}$, $Li_5ZrP_3O_{12}$, $Li_{14}Zn(GeO_4)_4$, $Li_4NbP_3O_{12}$, $Li_3Zr_2Si_2PO_{12}$, $Li_3Zr_2Si_2PO_{12}$ Suitable ceramic and glass ceramic lithium ion conductors useful as an impervious solid-state electrolyte material are described, for example in U.S. Pat. No. 4,985,317, and U.S. Patent Application Pub. No.: 2007/0087269 which is incorporated by reference herein in its entirety and for all purposes.

One particularly suitable impervious solid-state electrolyte material for use in a device for delivering lithium ions is a glass-ceramic of the following composition:

| Composition | Mol % |
| --- | --- |
| $P_2O_5$ | 26-55% |
| $SiO_2$ | 0-15% |
| $GeO_2 + TiO_2$ In which | 25-50% |
| $GeO_2$ | 0-50% |
| $TiO_2$ | 0-50% |
| $ZrO_2$ | 0-10% |
| $M_2O_3$ | 0 < 10% |
| $Al_2O_3$ | 0-15% |
| $Ga_2O_3$ | 0-15% |
| $Li_2O$ | 3-25% | and containing a predominant crystalline phase composed of $Li_{1+x}(M,Al,Ga)_x(Ge_{1-y}Ti_y)_{2-x}(PO_4)_3$ where $X \leq 0.8$ and $0 \leq y \leq 1.0$, and where M is an element selected from the group consisting of Nd, Sm, Eu, Gd, Tb, Dy, Ho, Er, Tm and Yb and/or and $Li_{1+x+y}Q_xTi_{2-x}Si_yP_{3-y}O_{12}$ where $0 < X \leq 0.4$ and $0 < Y \leq 0.6$, and where Q is Al or Ga.

The glass-ceramics are obtained by melting raw materials to a melt, casting the melt to a glass and subjecting the glass to a heat treatment. Such materials are available from OHARA Corporation, Japan and are further described in U.S. Pat. Nos. 5,702,995, 6,030,909, 6,315,881 and 6,485,622, which are incorporated herein by reference.

The conductivity of the solid-state electrolyte material of the barrier layer is preferably at least $10^{-7}$ S/cm and typically at least $10^{-6}$ S/cm. By employing a thin barrier layer (e.g., less than 10 microns thick), the requisiteness for high ionic conductivity (e.g., about $10^{-6}$ S/cm or higher) can be somewhat relaxed, but it is generally desirable that the solid-state electrolyte material is a fast ion conductor (FIC) of lithium (e.g., by FIC it is meant a conductivity of at least greater than $10^{-5}$ S/cm, more preferably greater than $10^{-4}$ S/cm or $10^{-3}$ S/cm, or higher).

The barrier layer is composed, in whole or in part, of the impervious solid-state electrolyte material, suitable examples of which have just been described above. For instance, the barrier layer can be a continuous, monolithic layer of just the impervious solid-state electrolyte material (e.g., as a sintered sheet or glass-ceramic plate). The barrier layer may also comprise additional materials to enhance performance or bring about the requisite properties of a barrier layer consistent with the principles described above: impervious barrier to fluids it contacts during normal device operation and storage, conductor of lithium ions which allows for their passage through the layer, and chemical compatibility with constituents from the mammalian side environment that it contacts.

In one embodiment, the solid-state electrolyte material can be distributed fairly uniformly throughout the barrier layer. For instance, the barrier layer may simply be a compositionally homogenous layer of the impervious solid-state electrolyte material. Moreover, even though the barrier layer is impervious, it is possible, and generally the case, that the impervious barrier layer contains some solid pores as well as defects—just so long as those pores or imperfections do not provide passage for fluids to move through and across the layer. In various embodiments the impervious barrier layer is dense having solid porosity less 20%, more preferably less than 10% and even more preferably less than 5%.

The barrier layer may comprise additional material components which may or may not be conductive to lithium ions. Such a composite structure may have a uniform or non-uniform distribution of components. For instance, various materials can be incorporated into a barrier layer to enhance or render imperviousness to the layer, generally improve mechanical properties, or facilitate processing. For instance, processing aids, such as ceramics (e.g., $Li_2O$) or glasses (e.g., silicates) can be incorporated to improve densification upon sintering the layer; and inert polymers (e.g., polyethylene, polypropylene) can be distributed within the layer to improve mechanical integrity. The barrier layer may further comprise a filler component material (e.g., an epoxy resin or glass) used to close off any through porosity.

The barrier layer is an impervious lithium ion conductor, which is to mean that the barrier layer prevents the transmission of fluids it contacts during normal device operation and storage from moving across the layer from one side of the layer to the other, while simultaneously allowing passage of lithium ions to electrically migrate across the layer when current flows from the counter electrode to the donor electrode (i.e., when electrons flow from the donor electrode to the counter electrode). When the field is turned off or the current flow is stopped, the barrier layer will no longer pass lithium ions until the electrical field is re-applied or current is allowed to flow again.

The barrier layer is generally a highly selective lithium ion conductor (e.g., showing at least one, preferably at least two, more preferably at least three or four or more orders of magnitude greater conductivity for lithium than for any other ion).

In certain embodiments the barrier layer can also be a single ion conductor having a lithium ion transference number of at least 0.95, or at least 0.99, or even at least 0.999. The transference number can be defined as the ratio of the lithium ion conductivity divided by the total conductivity of the layer, where the total conductivity includes the electronic conductivity plus the ionic conductivity of all ions of the layer. The intrinsic lithium ion conductivity of the barrier layer is generally at least as high as $10^{-7}$ S/cm, more preferably at least as high as $10^{-6}$ S/cm, and even more preferably at least $10^{-5}$ S/cm, $10^{-4}$ S/cm or $10^{-3}$ S/cm or higher.

In various embodiments, the barrier layer can be fabricated as a freestanding layer consistent with the principles, compositions and structures described above for a barrier layer. In accordance with the instant invention freestanding barrier layers can be fabricated by any technique known for fabrication of inorganic glasses, ceramics, and glass-ceramics in the form of a layer (e.g., a sheet, plate, membrane, etc.), including but limited to quenching a melt of the solid-state electrolyte material to form a glass, sintering (e.g., tape casting followed by sintering) of ceramic or glass-ceramic powders of the solid-state electrolyte material, and glass-ceramic processing of the solid-state electrolyte material, which generally entails the steps of melting and quenching to form a glass, followed by annealing and a crystallization heat treatment.

Freestanding layers consistent with the principles described above for a barrier layer and which can be usefully employed as a barrier layer or used in the fabrication of a barrier layer in protective architectures in accordance with the instant invention are disclosed in the following US patents and patent applications, all of which are hereby incorporated by reference herein: i) suitable barrier layers are described in U.S. Patent Application Pub. No.: US 2007/0087269 to Inda, where the barrier layer is generally referred to as a solid electrolyte sheet which is made by sintering an inorganic substance powder by first fabricating a greensheet comprising the inorganic substance powder followed by sintering; ii) suitable barrier layers are described in U.S. Pat. No. 4,985,317 to Adachi where the barrier layer is generally referred to as a solid electrolyte formed by sintering and solid electrolyte sheets; iii) suitable barrier layers are described in U.S. Patent Application Pub. No.: US 2007/0117026 to Kumar where the barrier layer is generally referred to as a sintered membrane and composite membrane fabricated by tape-casting followed by sintering of a glass or glass-ceramic powder; and iv) particularly suitable barrier layers are described in U.S. Pat. Nos. 5,02,995; 6,030,909; 6,315,881; and 6,485,622 to Fu and assigned to Kabushiki Kaisha Ohara, where the barrier layer is generally referred to as a glass-ceramic layer fabricated by glass-ceramic processing. Glass-ceramic layers as described above in the Fu references, are generally available from the Ohara Corporation.

Residual through porosity and/or the like, which may be present in a freestanding barrier layer, including any of the barrier layers incorporated by reference above, can be closed off by incorporating into any such through-pores a filler component (e.g., an epoxy resin), which effectively plugs-up the holes, rendering the layer impervious. Methods for closing off residual through porosity of a barrier layer, and associated filler compositions are described in applicant's commonly assigned U.S. Patent Application Pub. No.: US 2007/0172739 to Visco, and is hereby incorporated by reference herein for all that it discloses.

Protected Donor Electrode (Protected Anode)

In various arrangements the barrier layer in conjunction with the donor electrode can form a protected anode (protected donor electrode). Generally, the barrier layer is disposed adjacent to or near by the donor electrode, though not necessarily in contact with it, and positioned to isolate the electrode from mammalian side constituents. While in certain embodiments the barrier layer can be in direct contact with the donor electrode, additional layers can be incorporated on either side of the barrier layer, especially between the donor electrode and the barrier layer, to form what is referred to herein as a protective architecture.

The protective architecture can take on a variety of structural forms, it can be as simple as one discrete lithium ion-conducting barrier layer or it can be an assemblage of different lithium ion conductive material layers disposed on either side of the barrier layer and having a layered arrangement that brings about the requisite properties of a protective architecture as described above. Typically the architecture comprises at least two layers: a barrier layer and an interlayer—the interlayer incorporated to enhance the interface between the architecture and the donor electrode. The presence of the interlayer separates the barrier layer from the donor electrode, which relaxes the requirement that the barrier layer should be chemically compatible with the donor electrode, and this vastly broadens the possible choices of viable barrier layer materials, particularly that of the impervious solid-state electrolyte material.

Protective architectures useful for the devices of the instant invention may take on several forms. Some suitable protected anodes and their associated protective architectures are fully described in U.S. patent application Ser. No. 10/772,157 (Publication No. US20040197641 A1) and Ser. No. 10/824,944 (Publication No. US20050175894 A1) and their corresponding International Patent Applications WO 2005/038953 and WO 2005/083829, which are all incorporated by reference herein.

Figure 3A:
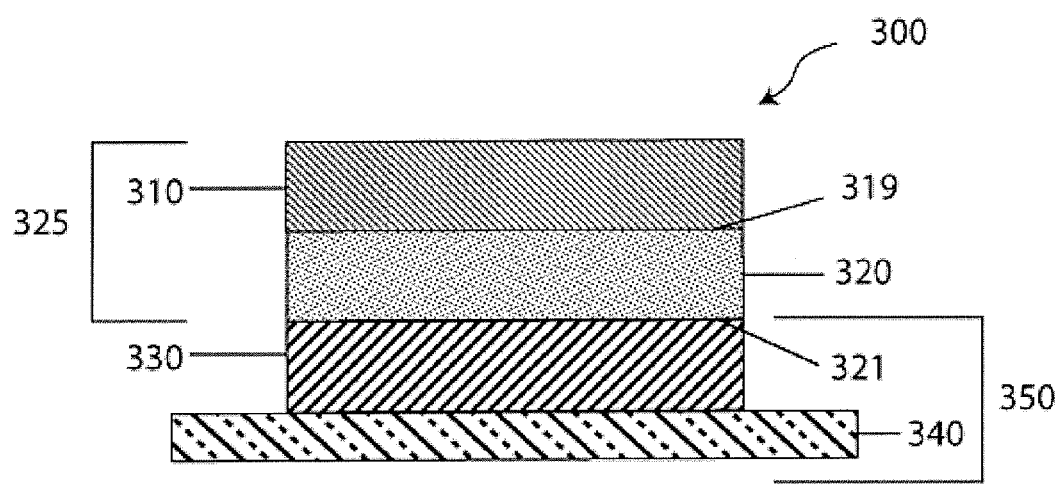
FIG. 3A schematically illustrates a protected donor electrode assembly 300 having a donor electrode 310 and a protective architecture 320.

Referring to the protected donor electrode assembly 300 illustrated in FIG. 3A, the protective architecture 320 in combination with the donor electrode 310 forms a protected donor electrode 325. The protective architecture has a first and a second face, the first face 319 is positioned in contact with and generally covers a first surface of the donor electrode 310. The second face 321 is adjacent and exposed to constituents on the mammalian side 350 of the architecture, which includes an optional electrolyte reservoir 330 and tissue 340. The architecture 320 and the reservoir 330 are positioned for lithium ion communication between the donor electrode 310 and the tissue 340. In one embodiment, the protective architecture can simply be a barrier layer, and as such the first surface of the barrier layer is adjacent to and in direct contact with the donor electrode and the second surface of the barrier layer makes up the second face of the architecture, and as such the second surface of the barrier layer is adjacent and exposed to the mammalian side environment 350.

This instant embodiment requires the barrier layer to be chemically compatible in contact with both the donor electrode and with the moisture rich environment(s) on the mammalian side, and/or aqueous media, when present. For highly reactive donor electrodes, this dual chemical compatibility requirement can be prohibitive, or at least may preclude the use of certain preferred solid-state electrolyte materials. Generally, chemical compatibility with the donor electrode is a critical limitation for some of the most preferred solid-state electrolyte materials from the perspective of having high conductivity, imperviousness and chemical compatibility with the mammalian side environment. Moreover, it is generally favorable, particularly for the fabrication of a free-standing barrier layer, that both surfaces of the layer have at least some ambient air stability.

The requirement of dual compatibility for the barrier layer can be restrictive, or at least may not provide opportunity for barrier layer optimization. As a result, in various embodiments protective architectures of the instant invention comprise an interlayer in contact with the donor electrode, and disposed between the barrier layer and the anode. By this expedient, the barrier layer can be formulated to optimize imperviousness, conductivity and chemical compatibility to moisture rich environments, ambient air and aqueous media without having to consider stability of the barrier layer in contact with the donor electrode, particularly the stability of its impervious solid-state electrolyte material.

Figure 3B:
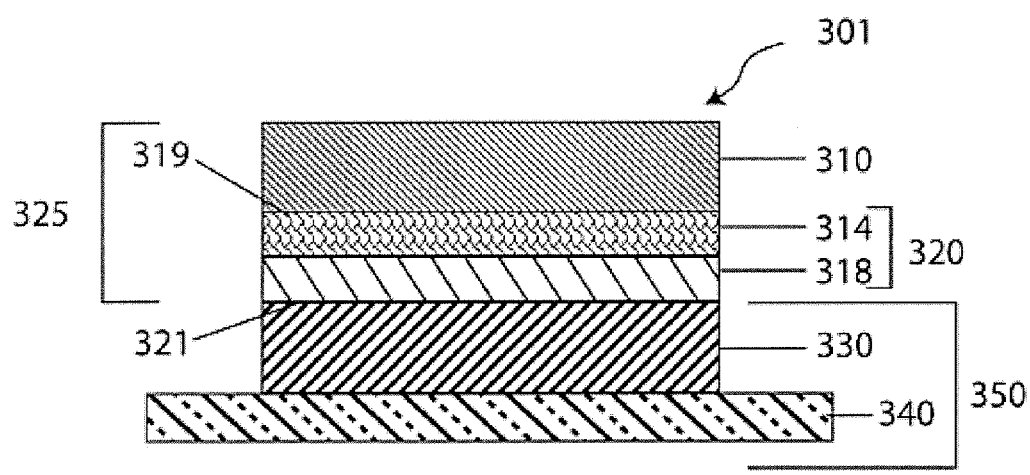
FIG. 3B illustrates a protected donor electrode assembly 301 with a protective architecture 320 having an interlayer 314 disposed between a barrier layer 318 and the donor electrode 310.

With reference to FIG. 3B, there is illustrated a donor electrode assembly 301 similar to that described above in FIG. 3A, except the protective architecture 320 of this embodiment has a barrier layer 318 and an interlayer 314. The second surface of the barrier layer still makes up the second face of the architecture, however in this embodiment the barrier layer is separated from the donor electrode 310 by a lithium ion conducting interlayer 314 chemically compatible and in contact with the donor electrode. In this embodiment, the surface of the interlayer in contact with the donor electrode makes up the first face of the architecture. In the instant embodiment, the architecture is shown having two layers, an interlayer and a barrier layer. Additional layers, between the barrier layer and the interlayer are contemplated in order to improve interfacial stability and protected donor electrode performance, generally. Because the interlayer 314 is positioned on the donor electrode side of the barrier layer 318, it is protected, along with the donor electrode 310, from exposure and contact with moisture rich environments and aqueous media on the mammalian side 350. This layered arrangement affords tremendous flexibility in terms of broadening the possible choices of interlayer materials, allowing the use of moisture sensitive, high conductivity, lithium ion conducting electrolytes with exceptional stability to electroactive lithium (e.g., lithium metal) to be used as, or part of, an interlayer. In fact, this architecture not only broadens the choice of solid electrolytes for use in a solid-interlayer, as will be described forthwith, it even enables the use of non-aqueous, lithium ion conducting, liquid electrolytes (referred to herein as anolyte) to be incorporated in the protective architecture—for instance, as a component in a, so-called, anolyte interlayer embodiment of a protective architecture.

The presence of the interlayer affords several advantages, including the opportunity to optimize the interface between the donor electrode and the architecture by employing moisture sensitive electrolytes having excellent stability in contact with the anode, while at the same time incorporating into the barrier layer a highly conductive impervious solid-state electrolyte material having exceptional chemical compatibility in contact with moisture rich environments. By this expedient, the dual compatibility conundrum, as described above, can be overcome and the barrier layer optimized for imperviousness and chemical compatibility with moisture rich environments.

Additional layers consistent with the principals of a protective architecture described above are contemplated between the interlayer and the barrier layer. A lithium ion conducting third layer may be incorporated between the interlayer and the barrier layer, to improve architecture performance and enhance overall chemical stability. More such layers can be incorporated between the barrier layer and the interlayer to further improve interface stability among the various layers and these embodiments are within the scope of the invention. However, while such additional layers are contemplated, it is generally preferable to limit the number of additional layers in order to reduce cost and complexity.

In certain embodiments it is contemplated that an open porous layer can be positioned on the mammalian side of the barrier layer. For instance, an open porous support structure (e.g., metal or ceramic) may be used to facilitate fabrication of a dense thin impervious barrier layer. When such a structure is incorporated into a protective architecture, the open pores of the support are generally filled with a liquid electrolyte capable of conducting lithium ions, such as an aqueous solution of the type present in the anode electrolyte reservoir.

Without limitation, the protective architecture comprising a barrier layer and additional layers such as an interlayer can be built up by first fabricating a freestanding barrier layer. The additional layers can then be placed between the freestanding barrier layer and the donor electrode, or the interlayer (or a third layer) can be deposited onto the freestanding barrier layer, followed by deposition of a lithium metal layer onto the interlayer. For instance, a solid interlayer can be deposited onto the barrier layer followed by deposition of lithium metal. Alternatively, a separator material (e.g., a micro-porous polymer) can be placed between the freestanding barrier layer and the donor electrode, the separator impregnated with a lithium ion conducting non-aqueous liquid electrolyte.

In various protective architecture embodiments, the interlayer is a solid lithium ion-conducting layer chemically compatible in contact with the donor electrode. In certain embodiments, the architecture can be fully solid-state comprising only solid lithium ion conducting layers, including a solid interlayer and a barrier layer. In certain embodiments, the solid interlayer is combined with the impervious barrier layer to form an ionically conductive protective composite. In accordance with such composites, the interface between the barrier layer and the solid interlayer can be discrete or it can have a graded transition. Details concerning the composition and fabrication of fully solid-state protective architectures comprising an ionically conductive protective composite, and which can be usefully employed to protect donor electrodes of the electrotransport devices of the instant invention are described in applicant's co-pending US Patent Applications having Publication No. US 20004/0126653, US 2004/0142244 and US 2004/0191617, and hereby incorporated by reference. The solid interlayer, as it is referred to herein, is generally referred to therein as a first component layer (or first layer material) and the barrier layer as it is referred to herein, is generally referred to therein as a second component layer (or a second layer material).

Referring back to the donor electrode assembly in FIG. 3B, the protective architecture 320 contains two layers, an interlayer 314 and a barrier layer 318 in contact with each other. If the interlayer is a solid, then the protective architecture is considered to be fully solid-state, and the combination of the solid-interlayer and the barrier layer is sometimes referred to as an ionically conductive protective composite. The solid-interlayer is both conductive to lithium ions and chemically compatible with the lithium donor electrode, and may not be chemically compatible with ambient air, and/or biochemical environment of tissue, and/or aqueous media.

For example, a wide variety of materials may be used as the solid-interlayer, in contact with the active metal. The solid-interlayer may be composed, in whole or in part, of active metal nitrides, active metal phosphides, active metal halides active metal sulfides, active metal phosphorous sulfides, or active metal phosphorus oxynitride-based glass. Specific examples include $Li_3N$, $Li_3P$, LiI, LiBr, LiCl, LiF, $Li_2S$—$P_2S_5$, $Li_2S$—$P_2S_5$—LiI and LiPON. The thickness of the interlayer is preferably about 0.1 to 5 microns, or 0.2 to 1 micron, for example about 0.25 micron.

In fabrication, lithium metal may be applied to these materials, or the solid-interlayer may be formed in situ by contacting precursors such as metal nitrides (e.g., transition metal nitrides), metal phosphides (e.g., transition metal phosphides), metal halides (e.g., transition metal halides), red phosphorus, iodine, nitrogen or phosphorus containing organics and polymers, halides and the like with lithium. Specific examples include P (e.g., red and black phosphorous), $Cu_3N$, $SnN_x$, $Zn_3N_2$, $FeN_x$, $CoN_x$, aluminum nitride (AlN), and silicon nitride. A particularly suitable precursor material is $Cu_3N$. The in situ formation of the interlayer may result from an incomplete conversion of the precursors to their lithiated analog. Nevertheless, such incomplete conversions meet the requirements of a first layer material for a protective composite in accordance with the present invention and are therefore within the scope of the invention.

The solid-interlayer or a precursor material can be formed directly onto the surface of a barrier layer using a variety of techniques. These include physical and chemical vapor deposition techniques including evaporation (including e-beam evaporation), sputtering and the like. This can be followed by deposition of lithium metal to form the protected donor electrode. Also, as noted above, the solid-interlayer may be formed in situ from the non-deleterious reaction of one or more precursors with the active metal electrode. For example, a $Li_3N$ interlayer may be formed on a Li anode by contacting $Cu_3N$ with the Li anode surface, or $Li_3P$ may be formed on a Li anode by contacting red phosphorus with the Li anode surface.

Also, a suitable solid-interlayer may include a material used to facilitate its use, for example, the residue of a thin wetting layer (e.g., Ag) used to prevent reaction between vapor phase lithium (during deposition) and LiPON when LiPON is used as a solid-interlayer material. When lithium is evaporated onto this structure, the Ag is converted to Ag—Li and diffuses, at least in part, into the greater mass of deposited lithium, and a protected lithium electrode is created. The thin Ag coating prevents the hot (vapor phase) lithium from contacting and adversely reaction with the LiPON solid-interlayer. After deposition, the solid phase lithium is stable against the LiPON. A multitude of such transient/wetting (e.g., Sn) and solid-interlayer material combinations can be used to achieve the desired result.

Another suitable lithium metal compatible interlayer may also include a polymer component to enhance its properties. For example, polymer-iodine complexes like poly(2-vinylpyridine)-iodine (P2VP-$I_2$), polyethylene-iodine, or tetraalkylammonium-iodine complexes can react with Li to form a LiI-based film having significantly higher ionic conductivity than that for pure LiI.

Fully solid-state protective architectures, in accordance with the present invention, can comprise additional solid lithium ion conducting layers incorporated between the solid-interlayer and the barrier layer. For instance, a LiPON layer (as a third layer) can be deposited (e.g., by RF sputter deposition) onto a barrier layer followed by deposition of a copper nitride layer (e.g., $Cu_3N$) followed by evaporation of lithium metal to form a lithium ion conducting reaction product interlayer in contact with the lithium metal donor electrode. The barrier-layer separated from the Li/$Cu_3N$ reaction product by the LiPON third layer which is typically in the range of 0.1 to 1 micron thick.

Compositions, components and methods of fabrication for or adaptable to the protective architectures and protected donor electrodes of the present invention are described in U.S. patent application Ser. No. 10/686,189, filed Oct. 14, 2003, and titled IONICALLY CONDUCTIVE COMPOSITES FOR PROTECTION OF ACTIVE METAL ANODES, and U.S. patent application Ser. No. 10/731,771, filed Dec. 5, 2003, and titled IONICALLY CONDUCTIVE COMPOSITES FOR PROTECTION OF ACTIVE METAL ANODES. These applications are incorporated by reference herein in their entirety for all purposes.

Fully solid-state protective architectures in accordance with this invention should have an inherently high ionic conductivity. In general, the lithium ionic conductivity of the composite is at least $10^{-8}$ S/cm, generally at least about $10^{-7}$ to $10^{-6}$ S/cm, and may be as high as $10^{-5}$ to $10^{-3}$ S/cm or higher. The thickness of the solid-interlayer should be enough to prevent contact between the barrier layer (or a third layer as such) and the anode. For example, the solid-interlayer can have a thickness of about 0.1 to 5 microns; 0.2 to 1 micron; or about 0.25 micron.

Another suitable architecture for protected donor electrodes in accordance with the instant invention is partially solid-state: composed of a barrier layer, as described above, and an interlayer comprising a liquid, lithium ion-conducting, non-aqueous electrolyte, generally referred to herein as anolyte (i.e., electrolyte about the anode). Partially solid-state protective architectures having an interlayer comprising anolyte and are described therein as having an ionically conductive protective interlayer architecture are disclosed in applicant's commonly assigned U.S. Pat. No. 7,282,295 and is hereby incorporated by reference herein. The anolyte interlayer as referred to herein, is generally described therein as a separator impregnated with an anolyte, and the barrier layer as referred to herein is generally described as a substantially impervious ionically conductive layer therein.

Referring back to the donor electrode assembly shown in FIG. 3B, if the interlayer 314 in contact with the donor electrode contains anolyte, then the architecture 320 is considered to be partially solid state. In accordance with this embodiment, the barrier layer 318 isolates the donor electrode 310 from constituents on the mammalian side of the architecture, and it also blocks the anolyte from moving across the architecture to the mammalian side. In this embodiment, the interlayer 314 comprises a separator layer impregnated with anolyte. The separator layer and the non-aqueous anolyte are chemically compatible with the lithium anode and in contact with the anode. The impervious barrier layer can be in contact with the interlayer (i.e., both the separator layer and the anolyte) as is shown in the figure, or additional layers can be disposed between the barrier layer and the anolyte interlayer. Generally, in partially solid-state protective architectures, the barrier layer is at least in contact with the anolyte of the interlayer. In certain embodiments, the partially solid-state architecture is composed of two layers, the barrier layer and the anolyte interlayer in contact and chemically compatible with each other.

The anolyte interlayer generally comprises a separtor layer impregnated, imbibed, filled, swelled or gelled with anolyte. The separator layer can be a porous solid, for instance a porous polymer, impregnated with anolyte. The interlayer can be a gel electrolyte, comprising a polymer gelled with anolyte. The interlayer can be a polymer separator swelled with anolyte, or any combination of the above. In a certain embodiment, the anolyte interlayer of a partially solid state protective architecture comprises a semi-permeable membrane, as a separator layer, impregnaged with anolyte. Suitable semi-permable separator layers include micro-porous polymers such as micro-porous polypropylene and/or micro-porous polyethylene, such as a Celgard micro-porous separator. In other embodiments, the anolyte interlayer is a gel electrolyte comprising a polymer such as but not limited to hexafluoropropylene-vinylidene fluoride copolymers (PVdf-HFP) and polyacrylonitrile compounds that are gelled with anolyte. In still other embodiments, the anolyte interlayer can be a lithium ion-conducting polymer that is swelled with a liquid, generally organic solvent, or the anolyte interlayer can be a polymer swelled with anolyte.

In these various embodiments, because the anolyte is in contact with highly reactive donor electrodes, the anolyte is non-aqueous. The anloylte may comprise an organic solvent and a supporting electrolyte salt or an inorganic ionic liquid. Generally the anolyte is an organic lithium ion-conducting electrolyte, generally in a liquid phase or gel phase. For example, the anolyte may include a solvent selected from the group consisting of organic carbonates, ethers, lactones, sulfones, etc., and combinations thereof, such as EC, PC, DEC, DMC, EMC, 1,2-DME or higher glymes, THF, 2MeTHF, sulfolane, and combinations thereof. 1,3-dioxolane may also be used as an anolyte solvent, particularly but not necessarily when used to enhance the safety of a cell incorporating the structure. When the anolyte is in the gel phase, gelling agents such as polyvinylidine fluoride (PVdF) compounds, hexafluoropropylene-vinylidene fluoride copolymers (PVdf-HFP), polyacrylonitrile compounds, cross-linked polyether compounds, polyalkylene oxide compounds, polyethylene oxide compounds, and combinations and the like may be added to gel the solvents. Suitable anolytes will also, of course, also include active metal salts, such as, in the case of lithium, for example, $LiPF_6$, $LiBF_4$, $LiAsF_6$, $LiSO_3CF_3$ or $LiN(SO_2C_2F_5)_2$.

Partially solid-state protective architectures in accordance with this invention should have an inherently high ionic conductivity. In general, the lithium ionic conductivity of the architecture is at least $10^{-8}$ S/cm, generally at least about $10^{-7}$ to $10^{-6}$ S/cm, and may be as high as $10^{-5}$ to $10^{-3}$ S/cm or higher.

In various further embodiments, additional layers can be incorporated between the separator layer and the barrier layer. For instance, the barrier layer may have a solid lithium ion conducting layer covering its first surface and in contact with the separator layer, or additional separator layers impregnated with anolyte are contemplated between the barrier layer and the interlayer.

It is also contemplated that the liquid interlayer may simply be a non-aqueous liquid electrolyte disposed between the barrier layer and the anode.

Electrolyte Reservoir

Referring back to FIG. 1, while it is contemplated that the protective architecture 104 may be placed in direct contact with the body surface, in certain embodiments, an electrolyte reservoir layer is disposed between the protected anode 110 and the tissue surface 200. The electrolyte reservoir layer 112, when present, comprises at least an electrolyte capable of supporting the electrical current, such as an aqueous solution containing a supporting electrolyte salt (e.g., sodium chloride (NaCl) or tetra-butylammonium (TBA) salts including TBA chloride). Generally the reservoir also comprises a material that is able to retain the supporting electrolyte solutions such as, but not limited to, polymer gels (e.g., a hydrogel) or polymer matrices imbibed with the supporting electrolyte. Examples of such reservoirs are disclosed in U.S. Pat. Nos. 4,383,529; 4,474,570; 4,722,726; and 7,150,975, which are incorporated herein by reference.

Preferably the reservoir should retain its general shape and inhibit water loss by evaporation. Polymers and gels suitable as a material to retain supporting electrolyte solutions are well known to those of skill in the art of iontophoretic devices. Suitable examples include, but are not limited to polyethylene oxides, CARBOPOL®, cellulose derivatives such as hydroxypropyl, methyl cellulose and hydroxyethyl cellulose, collagen, agar, pectin and the like; for instance, agar, in the range of 2 (w/v) to 4 (w/v) weight percent by volume.

In various embodiments the supporting electrolyte solution is generally an aqueous solution containing a biocompatible supporting salt, which is chemically inert and pharmacologically nontoxic, and preferably not readily absorbed through the skin. Suitable supporting salts include tetra-alkylammonium salts such as tetra-butylammonium (TBA) salts including TBA chloride, bromide, iodide or sulfate, as well as tetra-ethylammonium (TEA) salts including TEA hydrogen sulfate or hydrogen carbonate and combinations thereof. Generally, the supporting salt concentration will be optimized to provide sufficient conductance through the electrolyte. In some embodiments the supporting electrolyte salt may include a lithium salt, added to the electrolyte to optimize the delivery rate of the lithium metal cation through the skin. Suitable salts include LiCl, Li-carbonate, Li-nitrate. The concentration of the lithium salt dissolved in the electrolyte will depend on the application of the device and the desired treatment. In embodiments that utilize a Li salt in the electrolyte, the salt concentration can be optimized to provide high efficiency of lithium ion delivery.

The supporting electrolyte solutions may contain other chemical species which are known to those of skill in the art, to effect various properties of the electrolyte reservoir including surfactants, buffers, osmolarity adjusters (e.g., polyethylene glycols, sugars), antibiotics, penetration enhancers (e.g., alkanols), stabilizers, anti-fungal compounds such as paraben derivatives, enzyme inhibitors, preservatives, thickening agents.

Counter Electrode

The counter electrode (cathode) in ionic communication with the cathode electrolyte reservoir layer and/or in contact with the tissue surface completes the electrical circuit through the tissue and is generally chosen such that the cathode itself and any products of electro-reduction are innocuous to the subject being treated. The cathode may be any suitable iontophoretic cathode as described, for example, in U.S. Pat. Nos. 5,405,317 and/or 5,135,477 which are incorporated herein by reference for all that they contain.

By way of illustration, in certain embodiments, the cathode can be an inert electrode (e.g., a metal foil such as stainless steel), or more commonly a sacrificial electrode (e.g., Ag/AgCl). In various embodiments the cathode is also chosen for its ability to provide a galvanic couple in combination with the donor electrode to provide the electromotive driving force for the electrochemical reactions and to drive the lithium ion current across the body surface (e.g., the stratum corneum). The galvanic couple can also be used to provide electrical power for any optional device control circuitry. Thus, while certain embodiments, contemplate the use of a galvanic couple to drive lithium ion delivery without the use of an external power supply, the invention is not limited as such and also contemplates the use of an external power supply, such as a battery, to assist in driving the current and/or powering peripheral electronics.

In certain embodiments the counter electrode 120 is a sacrificial cathode that generally comprises a metallic salt in contact with a metal cathode. For example silver chloride in contact with metallic silver (Ag/AgCl electrode) or iron chloride in contact with metallic iron (Fe/FeCl electrode). In certain embodiments, the counter electrode is a Ag/AgCl cathode such as is known to those of skill in the art of iontophoretic drug delivery. In such instances, the supporting electrolyte generally contains a sodium chloride salt with a suitable buffer (e.g., sodium phosphate buffer). During device operation, the Ag/AgCl cathode is electrochemically reduced, as AgCl on the surface of the metallic silver electrode is reacted to give silver metal and chloride anion as follows:

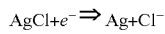
$AgCl + e^- \rightleftharpoons Ag + Cl^-$

The cathode electrolyte reservoir layer, when present, can be composed of similar materials as are suitable for the anode electrolyte reservoir layer, such as a polymer gel matrix or polymer gel (e.g., hydrogel). The supporting electrolyte solution employed in the cathode electrolyte reservoir layer depends, in part, on the type of counter electrode employed. Supporting electrolyte solutions that are suitable for cathodes useful for the instant invention are known in the art of iontophoretic drug delivery. Generally they are pharmacologically non-toxic and chemically inert. Suitable salts include, but are not limited to, sodium chloride, sulfates, nitrates, phosphates, citrates and mixtures thereof. The addition of a buffer is also useful. For example, when the cathode is a Ag/AgCl electrode the electrolyte solution can be an aqueous solution containing sodium chloride (e.g., a 0.1 molar salt solution).

Electronic Control and/or Power Source

With reference to FIG. 1 the device 100 can comprise an optional electronic control and/or power source unit 130 that can be used to control current and adjust drug delivery rate as well as provide power, for instance by means of a battery, to drive the electrical current of the device and to power device electronics. Moreover, in accordance with the instant invention, the number of coulombs of electrons passed from the anode to the cathode corresponds directly to the number of coulombs of Li ions liberated at the anode. As such the control circuit, by simply counting coulombs of electronic charge passed, can precisely record the amount of lithium metal ions liberated from the anode for delivery to the body surface. In some embodiments, the electrical circuitry may be as simple as a single precision resistor selected for a desired rate of drug delivery, or a set of resistors that can be toggled over the course of drug delivery to control the rate as a function of dose and time. In various embodiments the control unit can include a microprocessor to control current through the device in a pre-programmed fashion as a function of time. Such electrical components can be utilized to regulate the level, waveform, timing and other aspects of the electrical current and/or to adapt the current over time or in response to changes in conductivity of the tissue and/or device. Such electrical circuits are well known to those of skill in the art and are described, for example, in U.S. Pat. No. 5,533,971.

Alternative Electrode Arrangements

The arrangement between the cathode and the anode can take on any number of suitable formats. In the embodiment illustrated in FIG. 1 and FIG. 4 the anode and cathode are placed adjacent to each other in ionic communication with the skin in a side-by-side configuration separated by an air gap or insulating material.

Figure 4:
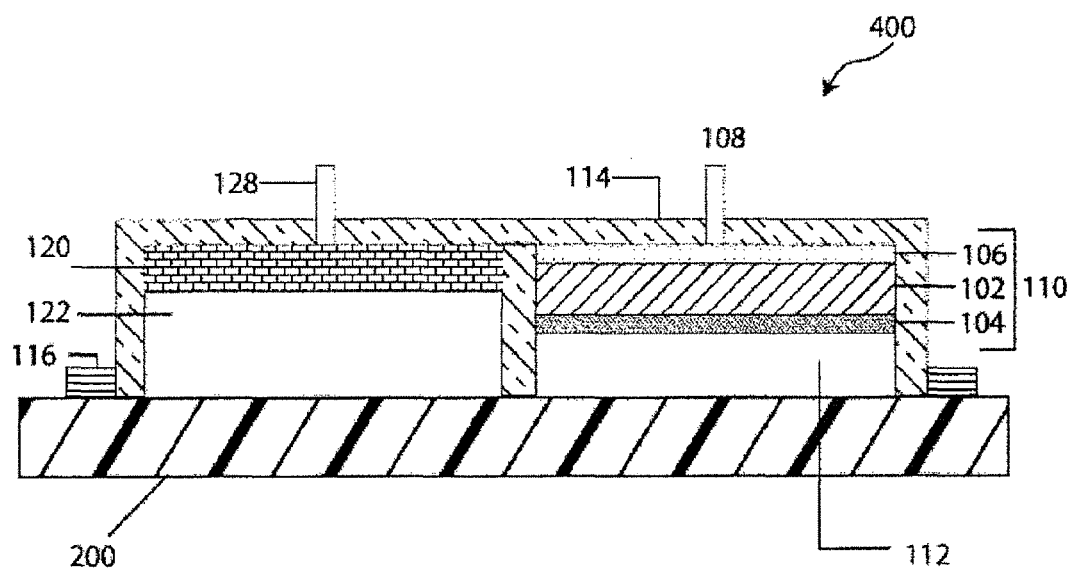
FIG. 4 schematically illustrates a cross sectional depiction of an electro-transport device 400 for delivery of lithium ions across a tissue surface 200. As shown in the figure, the device comprises a protected lithium anode comprising a lithium electrode 102, a protective membrane 104, and an optional current collector 106 (e.g., metal foil). Also shown is anode terminal connector 108, an optional electrolyte reservoir layer (e.g., hydrogel) 112, a cathode 120 (e.g., silver chloride electrode), an optional cathode electrolyte reservoir layer 122, and a cathode terminal connector 128. Also illustrated is a housing 114 for the device and an optional means 116 of affixing the device to a tissue surface (e.g., an adhesive).

Referring to FIG. 4, generally the electro-transport device will comprise a housing support structure made of a non-conductive material preferably made of a polymeric material that can be rigid, but is preferably flexible. For implantable devices, the housing will be fabricated from a biocompatible material.

The device can further include a means for affixing the device to a tissue (e.g., a skin) surface. Various means are known to those of skill in the art. One such approach utilizes a bio-compatible adhesive (e.g., polyisobutylene) around the periphery of the device to keep it attached to the body surface. Such adhesives are well known in the art of iontophoretic drug delivery systems.

In one embodiment, the lithium donor electrode comprises a stand-alone anode patch, as illustrated in FIGS. 2A and 2B, that can be incorporated into a drug delivery device by connecting it to a corresponding cathode patch or inserting it into an electro-transport device structure.

Figure 5A:
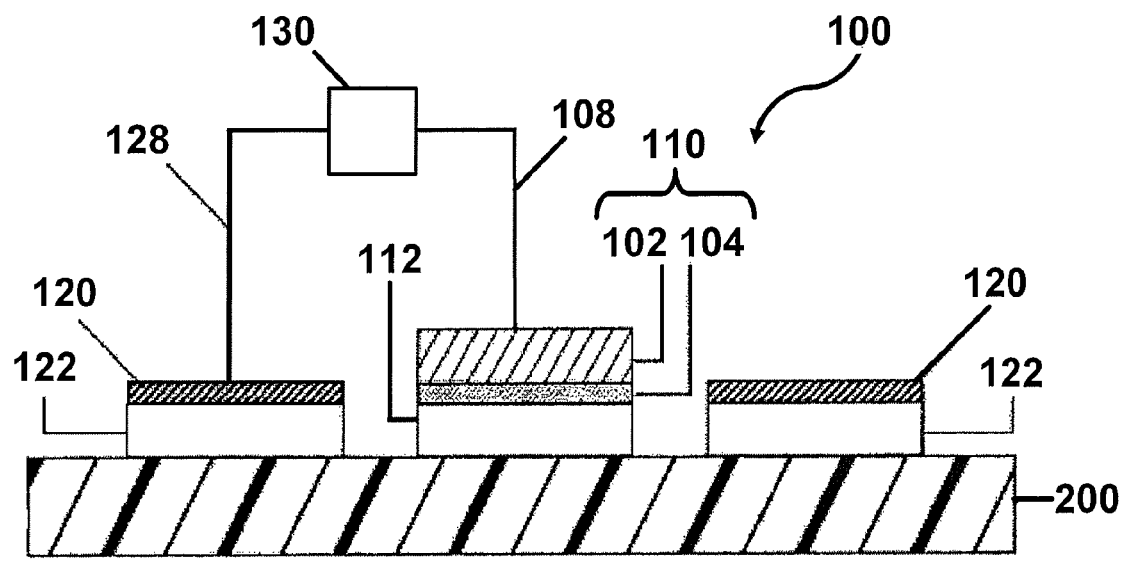
FIGS. 5A and 5B depict an alternative arrangement of electrodes in a device of the present invention.
Figure 5B:
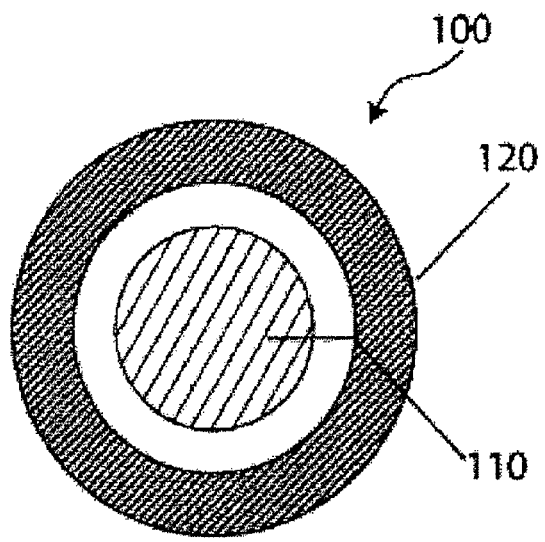

In another illustrative embodiment, the protected lithium anode and the cathode can be aligned adjacent to each other in a concentric ring fashion as shown in FIG. 5A (cross sectional view) and FIG. 5B (top down view). As shown in these figures, the counter electrode is adjacent to the protected lithium electrode and surrounds it around its outer periphery. The protected lithium electrode is of circular geometry. A spacer is placed between the donor electrode and the counter electrode, such as that described herein as an air gap or an insulating material. Alternatively, the anode and cathode may also swap positions. Moreover, the geometry is not limited to a circular embodiment, but includes other geometries such as rectangular and oval.

The foregoing embodiments are intended to be illustrative and not limiting. Using the teaching provided herein, other electrode arrangements will be available to one of skill.

Implantable or Penetrant Devices

In certain embodiments, the electro-transport devices of the present invention are provided as implantable devices that can be implanted within the body of the subject (e.g., subcutaneously, intraperitoneally, etc.). Implantation of the device improves patient compliance (an issue for subjects having a psychiatric disorder) and provides higher rates of lithium ion delivery, and facilitates precise control/regulation of lithium levels.

Implantable devices of the present invention typically comprise a housing that is hermetically sealed, contains all of the components of the device, and is manufactured from a biocompatible material. The implantable device further comprises one or more electrical contacts corresponding to the donor electrode(s) and the counter electrode(s). In certain embodiments the housing itself can act as one electrode (e.g., the counter electrode), while the other electrode (e.g., the donor electrode) is provided as a through feed electrically isolated from the rest of the housing or a contact area on the face of the housing also electrically isolated from the rest of the housing.

Suitable biocompatible materials are know to those of skill in the art (see, e.g. implantable defibrillator devices as describe, for example in U.S. Pat. Nos. 5,645,586, 4,481,953, 4,161,952, 4,934,049, and the like) and include, but are not limited to biocompatible metals (e.g., titanium, tantalum, stainless steel, and the like), biocompatible composite materials (e.g., ENDOLIGN™ from Invibio Ltd., bioceramic composites, etc.), biocompatible polymers (e.g., TEFLON®, silicone rubber, segmented polyurethane (e.g., BIONATE®), polycarbonate-urethane (e.g., Elasthane™), thermoplastic polyether urethane, silicone-polyether-urethane (e.g., PURSIL®), silicone-polycarbonate-urethane (e.g., CARBOSIL®), aliphatic thermoplastic silicone polyether urethane (e.g., PURSIL® AL), and the like), etc.

Methods and materials for providing sealed feed throughs are also well known to those of skill in the art (see, e.g., implantable defibrillator devices). One example is the use of KRYOFLEX® (P A & E, Wenatchee, Wash.) polycrystalline ceramics to hermetically sealing together materials used for electrical feed throughs in various polymeric casings.

Figure 6A:
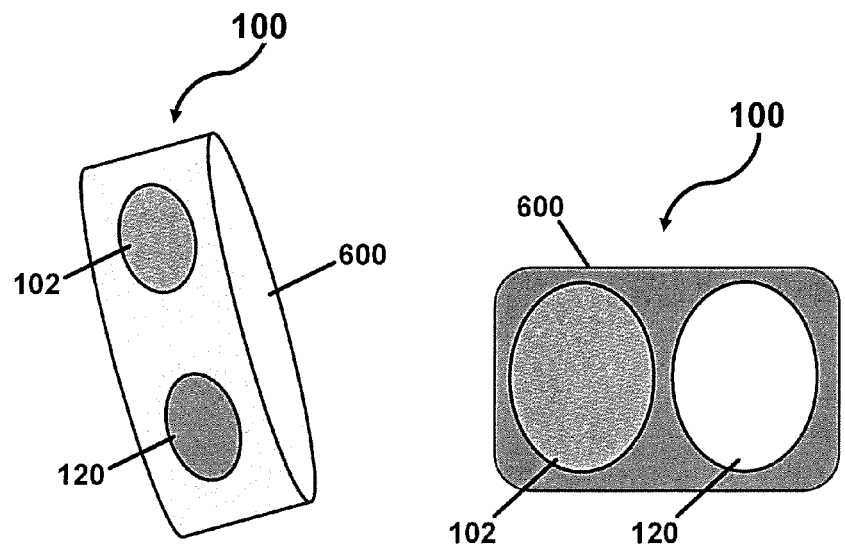
FIGS. 6A and 6B show illustrative configurations of an implantable electro-transport device.
Figure 6B:
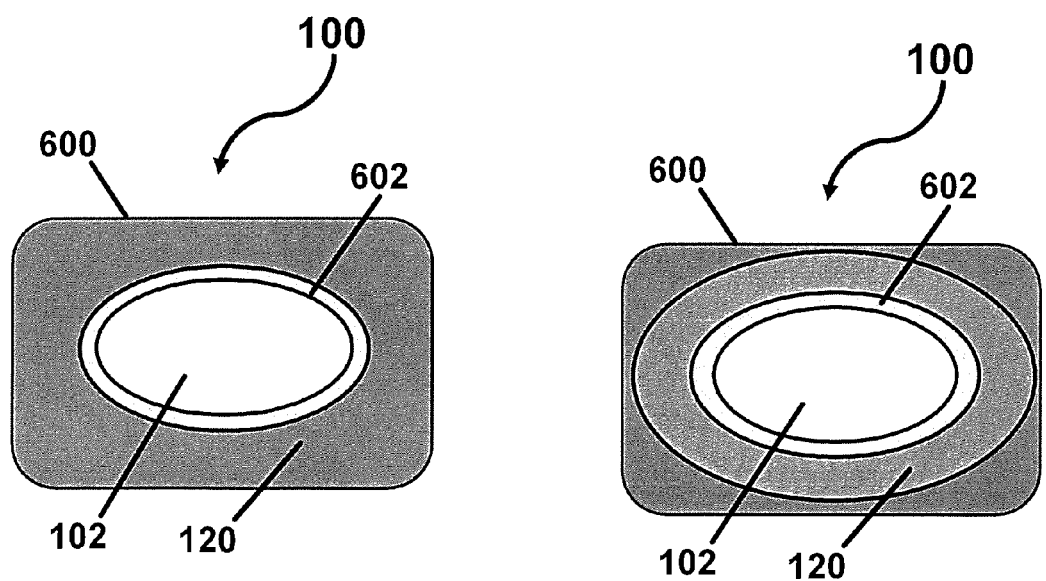

The implantable devices can be provided in any of a number of configurations as described herein (see, e.g., as illustrated in FIGS. 6A and 6B). In one configuration, illustrated in FIG. 6A, the device is encapsulated in a biocompatible non-conducting housing 600. The anode and cathode are provided as separate feed throughs.

In another configuration illustrated in FIG. 6B, right panel, the device is encapsulated by a non-conducting housing 600 and the anode 102 and cathode 120 are provided in an annular configuration (e.g., as illustrated in FIGS. 5A and 5B) separated by a non-conductor 602.

In certain embodiments, the housing is conducting and can act as the anode or cathode. As illustrated in FIG. 6B, left panel, the housing 600 is conducting and acts as a counter electrode 120. The anode 102 is electrically isolated from the housing by a non-conductor 620.

In various embodiments the implantable device can be passive, e.g., relying only on a galvanic couple to determine the potential. In certain embodiments the implantable device will provide a means for adjusting or permanently setting the current of the device. In such instances, the current level can be pre-set or manually set when the device is implanted, for example, when the rate of lithium ion delivery is determined in situ for the implanted device.

In various embodiments the implantable device further comprises an energy storage device (e.g., a battery, a capacitor, etc.), and optionally provides means for recharging while implanted (e.g., utilizing an induction charging unit). In certain embodiments the implantable device comprises a microcontroller and associated circuitry. The microcontroller can be coupled to a memory, e.g., by a suitable data/address bus where the operating parameters used by the microcontroller are stored and/or modified, as required, in order to customize the operation (ion delivery) to suit the needs of a particular patient. Such operating parameters define dosage, time course or daily cycles of delivery, and the like.

Advantageously, in certain embodiments, the operating parameters of the implantable device may be non-invasively programmed into the memory through a telemetry circuit in telemetric communication with an external device such as a programmer, a diagnostic system analyzer, and the like. In various embodiments the telemetry circuit can also provide status information relating to the operation of the device and/or the dosage regimen for the patient.

In certain embodiments the implantable device includes a physiologic sensor, that provides information on lithium ion level and/or current flow through the device and can be used to adjust lithium ion dosage rate according to state of the patient.

In various embodiments, this invention also contemplates "penetrant devices." Such devices can be applied to or affixed to a tissue surface (e.g., a skin surface), but are configured such that one or both electrodes penetrate into or thorough a tissue thereby providing more intimate communication with a tissue body, body cavity, or biological fluid.

It will be recognized that implantable devices, penetrant devices, and even in certain embodiments, topically applied devices according to this invention, can in certain cases deliver the lithium ions directly to a body fluid. Such body fluids, include but are not limited to blood, serum, lymph, oral fluid, mucus, cerebrospinal fluid, synovial fluid, and the like.

Kits

In another embodiment this invention provides kits for delivering lithium to a mammal. The kits typically comprise an electro-transport device as described herein. In certain embodiments the electro-transport device can be packaged in a container and/or can have removable protective caps or film, or other barrier over one or both electrodes that can readily be removed before use. Optionally, the kits can additionally contain an electrode cream, gel, ointment, fluid, or paste (e.g., a skin or other tissue compatible conductive medium) to promote good electrical contact (ion communication) between one or both electrodes and the surface to which the device is to be applied. Optionally, the cream, gel, ointment, fluid or paste can be provided already applied to the electrode surface(s) of the device. Optionally the kits can also include means (e.g., a solvent impregnated wipe or swab) for cleaning and/or disinfecting a tissue surface prior to application of the device. Optionally, the device can also include means (other than those that may be present on the device itself) for affixing the device to a tissue surface. Such means include, but are not limited to liquid, gel, paste adhesive and/or adhesive strips, and the like.

The kit can, optionally, further comprise one or more other agents typically administered to a subject being administered lithium. Such agents include, but are not limited to psychoactive medication for the subject, e.g., where the psychoactive medication is selected from the group consisting of neuroleptics (antipsychotics), sedatives and anxiolytics, antidepressants, a mood stabilizer, and anticonvulsant drugs. In certain embodiments the medication comprises a neuroleptic selected from the group consisting of trifluoperazine (Stelazine), pimozide (Orap), flupenthixol (Fluanxol), and chlorpromazine (Largactil), flupenthixol (Fluanxol), fluphenazine decanoate (Modecate), pipotiazine (Piportil L4), and haloperidol decanoate (Haldol LA). In certain embodiments the medication comprises a sedative and/or anxiolytic selected from the group consisting of a barbiturate, a benzodiazepine, and a non-barbiturate sedative. In certain embodiments the medication comprises an antidepressant selected from the group consisting of a tricyclic (e.g., amitriptyline (Elavil), imipramine (Tofranil), doxepin (Sinequan), clomipramine (Anafranil)), a monoamine oxidase inhibitors (e.g., phenelzine (Nardil) and tranylcypromine (Parnate)), a tetracyclic (e.g. maprotiline (Ludiomil)), trazodone (Desyrel) and fluoxetine (Prozac). In certain embodiments the medication comprises an additional mood stabilizer, e.g., carbamazepine.

In addition, the kits optionally include labeling and/or instructional materials providing directions (i.e., protocols) for the use of the devices described herein. In certain embodiments preferred instructional materials describe use the devices described herein for administering lithium to a subject in need thereof. The instructions optionally teach methods of applying the device to the subject, and/or methods of calibrating or adjusting the device to calibrate or adjust the rate of lithium delivery. The instructional materials may also, optionally, teach preferred dosages/therapeutic regimen, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Methods of Operation

The electrotransport devices of the instant invention can deliver lithium ions to a body component of a mammalian subject wherein the source of the lithium ions is stored in a lithium donor electrode as, or as a constituent of, an electroactive material. For instance the electroactive material can be electroactive lithium metal, for example a lithium metal foil. Because electroactive lithium is generally highly reactive, the devices of this invention incorporate a protective architecture that isolates the donor electrode from moisture rich environments such as ambient air and the biochemical environment of the body component for which lithium ions are intended for delivered (e.g., tissue such as skin, or tissue internal to the mammal, and aqueous media (e.g., bodily fluids) or aqueous solutions of an electrolyte reservoir, when present). In accordance with the instant invention, the lithium donor electrode in conjunction with the protective architecture forms a protected donor electrode. In the electrotransport devices of the instant invention, the protected lithium donor electrode (protected anode) is operably coupled to a counter electrode. In operation, the device is placed adjacent to the mammalian body component for which delivery of lithium ions is intended, such as an external body component like skin, or when the device is configured for implantable or subcutaneous delivery it is placed adjacent to an internal body component (e.g., dura matter or bodily fluids) of said mammal. Accordingly, when configured to the mammal, both the protected anode and the counter electrode of the device are placed in ionic communication with the body component for which lithium ions are intended for delivery.

In accordance with the devices of the instant invention, because the source of lithium is isolated from the body component (e.g., skin or bodily fluids) by the protective architecture, the source of lithium ions present in the donor electrode cannot passively diffuse from the donor electrode to the body component—rather their transfer across the protective architecture takes place under the influence of an electric field and only when a current is allowed to flow between the donor and counter electrodes via their operably coupling. By this expedient, devices of the instant invention which are configured for transdermal delivery provide improved safety and devices of the instant invention which are configured for subcutaneous delivery or are implanted within the mammal, not only provide improved safety—they are enabled because the lithium source (i.e., the lithium donor electrode) is removed from direct contact with bodily fluids and therefore does not passively and uncontrollably diffuse into the body component. In accordance with the devices of the instant invention, delivery of lithium ions can only take place when the device is activated for delivery by electrochemical oxidation of the donor electrode which generates the lithium ions for delivery, and those lithium ions thus generated are only able to transport across the architecture under an electric field (e.g., applied by a battery via device operable coupling or by a galvanic potential between the donor and counter electrodes) and when current flow is allowed to occur between the donor and counter electrodes (i.e., when electrons are allowed to move from the donor to the counter electrode). Accordingly, the delivery of lithium ions to the body component (or the electrolyte reservoir, when present) can be controlled by a switch which is part of the operable coupling of the device and which can alternately allow for or prevent current to flow between the donor electrode and the counter electrode: the switch can be opened to prevent current flow or closed to allow it. Moreover, the rate of the current can be controlled by control circuitry of the operable coupling in order to adjust the rate of lithium ion delivery to the mammalian subject. Furthermore, the devices of the instant invention can include control circuitry that is able to count coulombs passed from the donor electrode to the counter electrode in order to monitor the amount of lithium that has been delivered from the donor electrode to the body component or transferred to the electrolyte reservoir, when present.

The foregoing embodiments are intended to be illustrative and not limiting. Using the teaching provided herein other device configurations and methods for transporting lithium will be available to one of skill in the art.

EXAMPLE

The following example is offered to illustrate, but not to limit the claimed invention.

Figure 7:
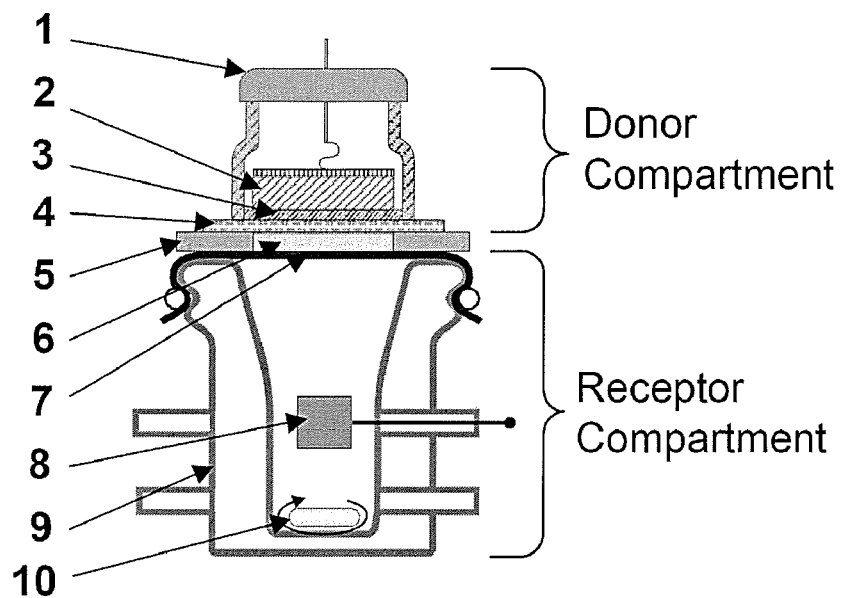
FIG. 7 shows a schematic cross section of a Li—AgCl cell for measuring in-vitro lithium delivery through skin (see, Example 1). The illustration shows the cap 1, lithium foil 2, non-aqueous interlayer 3, glass-ceramic plate 4, support 5, aqueous gel 6, skin 7, silver chloride cathode 8, water-jacketed glass cell 9, and stir bar 10.

Delivery of Li Ions Through Skin Using a Device Employing Li Metal Foil as a Source of Lithium Ions Lithium ion flow-through an in vitro cell having a receptor compartment and a donor compartment separated by a pig skin was used to demonstrate electro-transport of lithium using an illustrative embodiment of a device according to the present invention. The schematic cross-section of the cell is shown in FIG. 7. The glass receptor compartment was similar to one described by Phipps et al. (1988) *Solid State Ionics* 28-30: 1778-1783, for ionophoretic drug delivery experiments. The receptor compartment was filled with RPMI-1640 Medium (Sigma Aldrich). The antibiotic gentamicin sulphate was added to the receptor compartment fluid to inhibit bacterial growth.

Pig skin used in our experiments had a thickness of 0.65 mm. The prepared skin was stored in RPMI-1640 medium overnight before the start of the experiment. The skin was placed on the receptor chamber and kept in place and stretched out with an O-ring around the neck of the chamber. The visceral surface of the skin was in contact with the receptor fluid.

A square 1 cm×1 cm silver chloride cathode with a capacity of approximately 40 mAh was introduced into the receptor chamber through a port. A multi-channel peristaltic pump was used to create a flow of the RPMI-1640 medium through receptor compartments of several cells. In our experiments we used a flow rate of 2.1 mL/hr. Periodic sampling of the receptor compartment fluid was performed automatically. The temperature inside the water-jacketed receptor compartment was kept at 37° C. The fluid inside the receptor compartment was stirred with a magnetic stir bar.

The donor chamber was positioned over the skin. It contained Li metal foil and a protective architecture enabling the use of Li in an aqueous environment. The protective architecture comprised a 150 micron thick barrier layer composed of a glass ceramic solid electrolyte plate (AG-01 material from OHARA Corporation with ionic conductivity of ~$10^{-4}$ S/cm) and an anolyte interlayer located between the Li surface and the glass ceramic plate barrier layer. A square 1"×1" glass ceramic plate was bonded to the end of a Pyrex glass tube (OD of 25 mm, wall thickness of 1.5 mm) with an epoxy adhesive Hysol E 120 HP, which is stable in both aqueous and non-aqueous electrolytes.

The Li electrodes were fabricated by cutting ⅝" diameter circular discs from Li foil having 6 mm in thickness. The Li discs were pressed onto a Ni mesh current collector having a Ni foil tab. An anolyte interlayer between the Li foil and the glass ceramic plate consisted of a microporous membrane filled with a non-aqueous electrolyte. The non-aqueous electrolyte was 1 M $LiClO_4$ in propylene carbonate. The microporous membranes were made of 25 μm thick Celgard 3401 separator material and placed inside the Pyrex tube against the glass-ceramic plate. The top of the donor chamber containing Li metal anode was hermetically sealed with the epoxy adhesive Hysol E 120 HP. In order to ensure mechanical and electrical continuity between the surface of the glass ceramic plate and the skin, we placed a 1 mm layer of aqueous gel electrolyte between them. The agar gel electrolyte contained 2% agar and 20% tetrabutylammonium chloride by weight. Its specific ionic conductivity determined by the AC method was equal to $2.5 \times 10^{-2}$ S/cm and the resistance of the gel electrolyte layer did not exceed 4 ohm·cm².

The donor-acceptor chamber assembly was kept in place using a clamp. We ran Li delivery experiments in constant current mode simultaneously in two cells. The ionophoretic current density was 0.1 mA/cm² in the 1st cell and 0.2 mA/cm² in the 2nd cell. We used a PAR 273A potentiostat as a constant current source. Li content in the fluid samples taken from receptor compartment was analyzed by ICP-MS.

Figure 8:
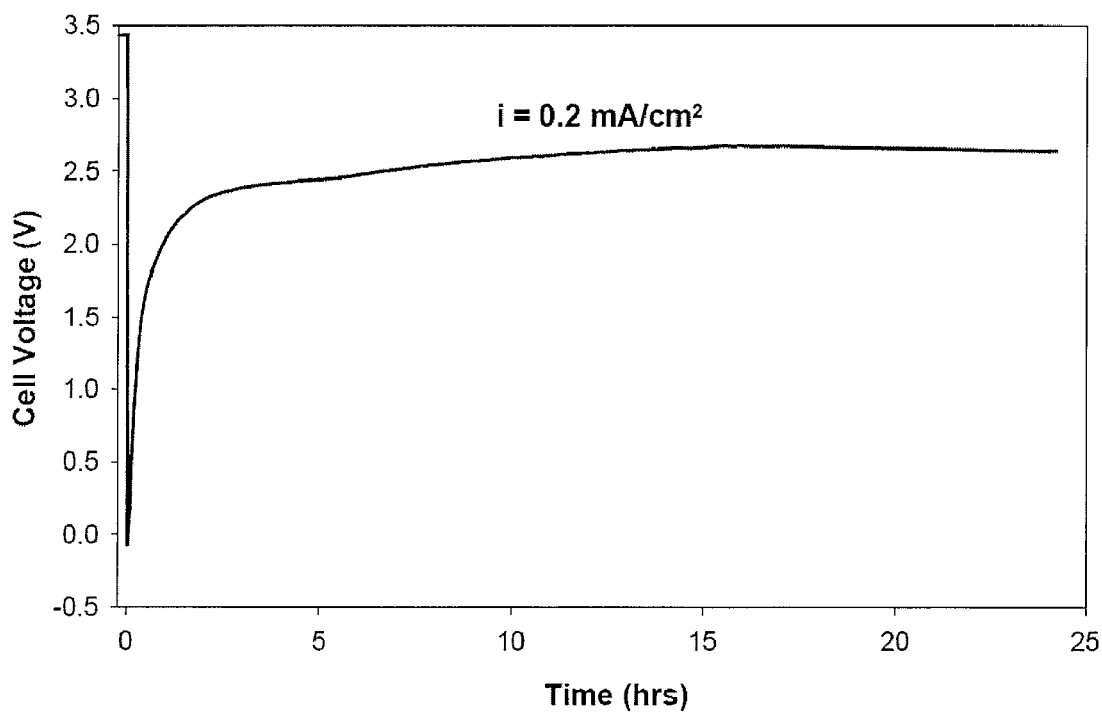
FIG. 8 shows the voltage response to anode current step in the cell shown in FIG. 7 employing pig skin.

FIG. 8 illustrates the change in voltage between the Li metal anode and the silver chloride cathode as anode current was passed through the cell. Initial cell polarization was very large: at a current density of 0.2 mA/cm² the cell voltage dropped slightly below 0 volts. With time cell voltage recovered and reached a steady state value of ~2.64 V. This behavior is typical for skin under current and is attributable to a decrease in skin resistance.

Figure 9:
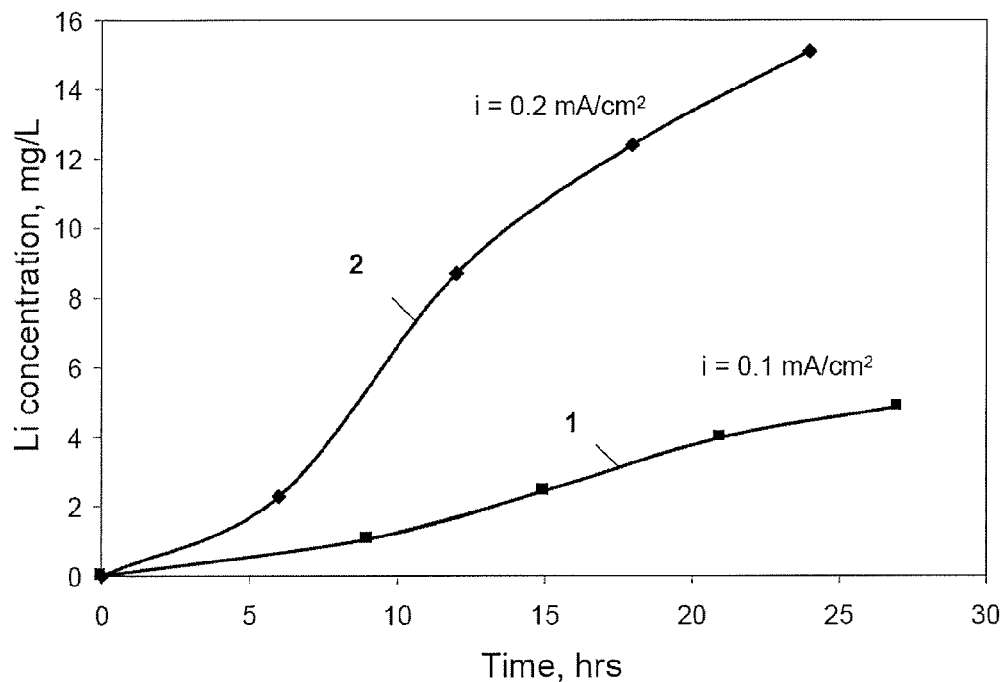
FIG. 9 shows the concentration of Li in the receptor chamber resulting from Li delivered through pig skin at different currents.

Over the duration of the experiment (27 hrs at a current density of 0.1 mA/cm² and 24 hrs at a current density of 0.2 mA/cm²), receptor fluid samples were taken and analyzed. Analysis of the receptor solution before current passing indicated that initial Li content did not exceed 6 μg/L. FIG. 9 shows that Li content in the samples gradually increased over time and was significantly larger for the rate of 0.2 mA/cm² than for 0.1 mA/cm².

Figure 10:
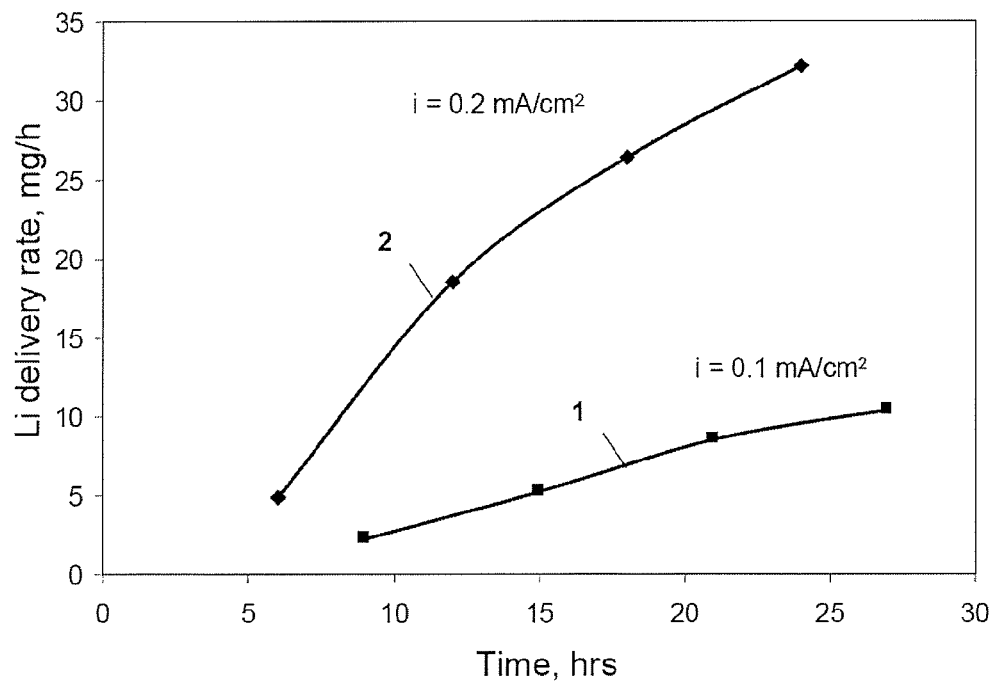
FIG. 10 shows the Li delivery rate through pig skin as measured in the cell shown in FIG. 7.

The plot of Li delivery rate vs. time for both current densities is shown in FIG. 10. The rate of Li delivery into the receptor compartment was calculated as a product of Li concentration and the flow rate of the receptor fluid.

It is believed that this example is the first demonstration of effective Li ion delivery through skin using a device employing Li metal foil as a source of Li ions.

Conclusion

New and novel devices and methods for administering lithium (Li) ions to a mammalian subject have been described.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An electrotransport device for delivering therapeutic lithium ions to a mammalian subject, said device comprising:
   a solid lithium donor metal electrode that is both a source of the therapeutic ions and an anode of a galvanic couple formed with a cathode applied to a body component of the mammalian subject that provides an electro-motive force to drive the ions of the lithium donor metal electrode into the subject;
   a lithium ion conductive protective architecture having a first and second face, said first face positioned on the donor electrode, and said second face adjacent to the body component of said mammalian subject, the architecture comprising a barrier layer substantially impervious to aqueous fluids;
   a counter electrode comprising the cathode operably coupled to said anode, wherein the operable coupling comprising the galvanic couple formed by the anode and the cathode generates an open circuit voltage of at least 2V;
   wherein the device does not comprise a reservoir containing a drug other than the therapeutic ions of the anode; and wherein the device is configured for self-powered lithium ion delivery from the lithium metal of the donor electrode to the body component.

2. The device of claim 1 wherein an electrochemical potential of the lithium donor electrode versus a standard hydrogen electrode (SHE) is more negative than about −2 V vs. SHE.

3. The device of claim 1, wherein said cathode generally comprises a metallic salt in contact with a metal cathode.

4. The device of claim 3, wherein said cathode is an Ag/AgCl electrode.

5. The device of claim 1, wherein the barrier layer comprises an inorganic, impervious solid-state electrolyte material that is intrinsically conductive to lithium ions.

6. The device of claim 5, wherein the inorganic solid-state electrolyte material is selected from the group consisting of glassy or amorphous materials, ceramics and glass-ceramics.

7. The device of claim 5, wherein the inorganic, solid-state electrolyte material is polycrystalline.

8. The device of claim 7, wherein the inorganic solid-state electrolyte material is a ceramic or glass-ceramic selected from the group consisting of lithium metal phosphates and lithium metal oxides.

9. The device of claim 8, wherein the ceramic or glass-ceramic is a lithium metal phosphate of the type $LiM_2(PO_4)_3$ where M is selected from the group consisting of Ge, Ti, Sn, Hf and Zr.

10. The device of claim 8, wherein the ceramic or glass-ceramic is a lithium metal phosphate of the type $Li_{1+x}M_x(Ti, Ge, Hf)_{2-x}(PO_4)_3$ where M is selected from the group consisting of Fe, Ga, Al, and rare earth elements, where $0.1 \leq x \leq 1.9$.

11. The device of claim 8, wherein the ceramic or glass-ceramic is a lithium metal phosphate of the type $Li_{1+x}M_x(Ti, Ge, Hf)_{2-x}(PO_4)_3$ where M is selected from the group consisting of Fe, Ga, Al, and rare earth elements, where x is about 3.

12. The device of claim 8, wherein the ceramic or glass-ceramic is $Li_{1+x+y}(Al,Ga)_x(Ti, Ge, Hf)_{2-x}Si_yP_{3-y}O_{12}$ where $0.1 \leq x \leq 1$ and $0.1 \leq y \leq 1$.

13. The device of claim 8, wherein the ceramic or glass-ceramic is $Li_{1+x+y}(Al,Ga)_x(Ti, Ge)_{2-x}Si_yP_{3-y}O_{12}$ where $0.1 \leq x \leq 1$ and $0.1 \leq y \leq 1$.

14. The device of claim 8, wherein the ceramic or glass-ceramic is $Li_{1+x+y}Al_xTi_{2-x}Si_yP_{3-y}O_{12}$ where $0.1 \leq x \leq 1$ and $0.1 \leq y \leq 1$.

15. The device of claim 5 wherein the inorganic solid-state electrolyte material is a glass-ceramic of the following composition:

| Composition | Mol % |
| --- | --- |
| $P_2O_5$ | 26-55% |
| $SiO_2$ | 0-15% |
| $GeO_2 + TiO_2$ | 25-50% |
| In which $GeO_2$ | 0-50% |
| $TiO_2$ | 0-50% |
| $ZrO_2$ | 0-10% |
| $M_2O_3$ | 0-10% |
| $Al_2O_3$ | 0-15% |
| $Ga_2O_3$ | 0-15% |
| $Li_2O$ | 3-25% | and containing a predominant crystalline phase composed of $Li_{1+x}(M,Al,Ga)_x(Ge_{1-y}Ti_y)_{2-x}(PO_4)_3$ where $X \leq 0.8$ and $0 \leq Y \leq 1.0$, and where M is an element selected from the group consisting of Nd, Sm, Eu, Gd, Tb, Dy, Ho, Er, Tm and Yb and/or $Li_{1+x+y}Q_xTi_{2-x}Si_yP_{3-y}O_{12}$ where $0 < X \leq 0.4$ and $0 < Y \leq 0.6$, and where Q is Al or Ga.

16. The device of claim 5, wherein the barrier layer has a lithium ion conductivity of at least $10^{-6}$ S/cm.

17. The device of claim 5, wherein the barrier layer has a lithium ion transference number of at least 0.99.

18. The device of claim 5, wherein said protective architecture further comprises a lithium ion conducting interlayer that is in contact and chemically compatible with the donor electrode, and in ionic communication with the barrier layer.

19. The device of claim 18, wherein the barrier layer and the interlayer are in contact and chemically compatible with each other.

20. The device of claim 18, wherein the interlayer comprises a lithium ion conducting anolyte.

21. The device of claim 20, wherein the anolyte of the interlayer is a non-aqueous, lithium ion conducting, liquid electrolyte.

22. The device of claim 21, wherein the anolyte interlayer further comprises a semi-permeable membrane impregnated with the non-aqueous liquid electrolyte.

23. The device of claim 22, wherein the semi-permeable membrane is a micro-porous polymer.

24. The device of claim 21, wherein the anolyte interlayer comprises a gel imbibed with the non-aqueous liquid electrolyte.

25. The device of claim 21 wherein the anolyte interlayer comprises a polymer swelled with the non-aqueous liquid electrolyte.

26. The device of claim 20 wherein the anolyte comprises an organic solvent.

27. The device of claim 20 wherein the anolyte interlayer has an ionic conductivity of at least $10^{-5}$ S/cm.

28. The device of claim 1, wherein said donor electrode is a lithium or lithium alloy electrode; said counter electrode comprises an Ag/AgCl electrode; and said protective architecture comprises the impervious barrier layer comprising a solid-state electrolyte material selected from the group consisting of glassy or amorphous lithium ion conductors, ceramic lithium ion conductors, and glass-ceramic lithium ion conductors; and said operable coupling comprises a current regulator.

29. The device of claim 1, wherein the body component is a skin surface and the device is configured for application to the skin surface of said mammalian subject.

30. The device of claim 1, wherein said device is encased in a biocompatible matrix or polymer compatible with implantation in the mammalian subject.

31. The device of claim 1, wherein said device is encased in a biocompatible matrix or polymer compatible with subcutaneous implantation.

32. The electrotransport device of claim 1 further provided in a kit for transdermal delivery of lithium, said kit comprising:

a container containing said electrotransport device.

33. The electrotransport device of claim 1, wherein said barrier layer is intrinsically conductive to lithium ions and consists essentially of a solid electrolyte selected from the group consisting of glassy or amorphous, ceramic and glass-ceramic material.

34. The electrotransport device of claim 1, wherein said barrier layer consists essentially of a ceramic or glass-ceramic solid electrolyte material that is intrinsically conductive to lithium ions.

35. The electrotransport device of claim 34, wherein said barrier layer consists essentially of the solid electrolyte material having the following composition:

| Composition | Mol % |
|---|---|
| $P_2O_5$ | 26-55% |
| $SiO_2$ | 0-15% |
| $GeO_2 + TiO_2$ | 25-50% |
| In which $GeO_2$ | 0-50% |
| $TiO_2$ | 0-50% |
| $ZrO_2$ | 0-10% |
| $M_2O_3$ | 0-10% |
| $Al_2O_3$ | 0-15% |
| $Ga_2O_3$ | 0-15% |
| $Li_2O$ | 3-25% | and containing a predominant crystalline phase composed of $Li_{1+x}(M,Al,Ga)_x(Ge_{1-y}Ti_y)_{2-x}(PO_4)_3$ where $X \leq 0.8$ and $0 \leq Y \leq 1.0$, and where M is an element selected from the group consisting of Nd, Sm, Eu, Gd, Tb, Dy, Ho, Er, Tm and Yb and/or $Li_{1+x+y}Q_xTi_{2-x}Si_yP_{3-y}O_{12}$ where $0 < X \leq 0.4$ and $0 < Y \leq 0.6$, and where Q is Al or Ga.

36. The electrotransport device of claim 1, wherein said aqueous fluids are liquids selected from the group consisting of aqueous media and bodily fluids.

37. The electrotransport device of claim 1, wherein said aqueous fluids are aqueous liquids.

* * * * *